(12) United States Patent
Cyko et al.

(10) Patent No.: US 11,607,318 B2
(45) Date of Patent: Mar. 21, 2023

(54) UNICONDYLAR TIBIA IMPLANTS

(71) Applicant: Smith & Nephew, Inc., Memphis, TN (US)

(72) Inventors: Christopher Ray Cyko, Memphis, TN (US); Jason Sean Jordan, Hernando, MS (US)

(73) Assignee: Smith & Nephew, Inc., Memphis, TN (US)

( * ) Notice: Subject to any disclaimer, the term of this patent is extended or adjusted under 35 U.S.C. 154(b) by 325 days.

(21) Appl. No.: 17/003,542

(22) Filed: Aug. 26, 2020

(65) Prior Publication Data

US 2020/0390560 A1 Dec. 17, 2020

Related U.S. Application Data

(63) Continuation of application No. 16/301,661, filed as application No. PCT/US2017/032863 on May 16, 2017, now Pat. No. 10,786,358.

(Continued)

(51) Int. Cl.
*A61F 2/38* (2006.01)
*A61F 2/30* (2006.01)

(52) U.S. Cl.
CPC .... *A61F 2/389* (2013.01); *A61F 2002/30131* (2013.01); *A61F 2002/30187* (2013.01);
(Continued)

(58) Field of Classification Search
CPC . A61F 2/389; A61F 2/3868; A61F 2002/3895
See application file for complete search history.

(56) References Cited

U.S. PATENT DOCUMENTS

2003/0060884 A1   3/2003 Fell et al.
2003/0060888 A1   3/2003 Fell et al.
(Continued)

FOREIGN PATENT DOCUMENTS

WO   2007090784 A1   8/2007

OTHER PUBLICATIONS

Notice of Reasons for Rejection, Office Action for JP Application No. 2018-555487, dated Apr. 5, 2021, original and translated documents, 15 pages.

(Continued)

*Primary Examiner* — Jason-Dennis N Stewart
(74) *Attorney, Agent, or Firm* — KDB Firm PLLC

(57) ABSTRACT

Unicondylar tibia implant devices having a bone-facing, distal side that can be detailed with cement fixation features and may include any of or a plurality of grooves, pegs, fins, rails, cavities, and/or coating whereby the geometry of the implant device improves implant-to-cement or cement-to-bone fixation characteristics exceeding that of a traditional flat surface. The implant device may also include a proximal side facing away from the bone-facing, distal side and having a geometry that provides either articulation with (cartilage and meniscal substituting) or receipt of a secondary device coupleable to the implant device on the distal side of the secondary device that features an away-from-bone facing articulating feature. Additionally, the geometry of the implant device in anterior-posterior and medial-lateral directions, among other directions, provides a variety of improvements relative to currently available devices.

20 Claims, 11 Drawing Sheets

Related U.S. Application Data

(60) Provisional application No. 62/337,020, filed on May 16, 2016.

(52) U.S. Cl.
CPC ............... *A61F 2002/30708* (2013.01); *A61F 2002/30878* (2013.01); *A61F 2002/30884* (2013.01); *A61F 2002/30892* (2013.01); *A61F 2002/3895* (2013.01)

(56) References Cited

U.S. PATENT DOCUMENTS

| | | |
|---|---|---|
| 2003/0100953 A1 | 5/2003 | Rosa et al. |
| 2004/0006393 A1 | 1/2004 | Burkinshaw |
| 2009/0299481 A9 | 12/2009 | Romagnoli |

OTHER PUBLICATIONS

Office Action, decision of rejection, for Chinese application No. 201780026656.2, dated Jul. 26, 2021, original and translated documents, 10 pages.
First Office Action for Chinese Patent Application No. 201780026656.2, dated Feb. 25, 2020.
International Search Report; European Patent Office; International Application No. PCT/US2017/032863; dated Aug. 31, 2017; 5 pages.
Written Opinion of the International Searching Authority; European Patent Office; International Application No. PCT/US2017/032863; dated Aug. 31, 2017; 5 pages.
Australian Examination report No. 1 for standard patent application No. 2017268219, dated Mar. 3, 2021, 4 pages.
Chinese Office Action for Application No. 201780026656.2, dated Dec. 9, 2020, 17 pages [original and translated].
Communication pursuant to Article 94(3) for EP Application No. 17726414.0, dated Dec. 14, 2020, 5 pages.

UNICONDYLAR TIBIA IMPLANTS

CROSS-REFERENCE TO RELATED APPLICATIONS

This application is a continuation of U.S. patent application Ser. No. 16/301,661, filed Nov. 14, 2018, which application is a U.S. National Phase of International PCT Application No. PCT/US2017/032863, filed May 16, 2017, which claims the benefit of U.S. Provisional Application No. 62/337,020, filed May 16, 2016, the contents of each application hereby incorporated by reference in their entirety.

BACKGROUND

Embodiments of the present application generally relate to implant devices for unicondylar knee arthroplasty. More particularly, but not exclusively, embodiments of the present application relate to anatomically shaped tibial implant devices for unicondylar knee arthroplasty.

Partial (unicondylar) knee arthroplasty, also referred to as unicompartmental knee replacement or partial knee replacement, is a procedure in which one of either the medial or lateral compartments of the distal femur and/or the proximal tibia can be replaced with an implant device. Typically, implant devices used for partial knee arthroplasty are designed to at least attempt to anatomically fit the proximal tibia anatomy of the patient. Moreover, at least certain types of implant devices used for partial knee arthroplasty have been designed to be interchangeable between compartment/hand, such that the opposite hand/compartment can be used as a secondary placement recommendation. For example, in certain instances, an implant device that is designed for use on the medial compartment can be implanted on the lateral compartment of the opposite hand.

Such devices however can suffer from a number of issues, including issues relating to reliability, performance, and/or wear of the implant device. For example, implantation on the lateral compartment of a tibia implant device that is designed for use on the medial compartment of the opposite hand can adversely impact the performance of the implant device, as there can be a lack of anatomic conformance to the lateral geometry of the resected tibia. Further, poor tibial fit on both the medial and lateral tibial plateaus can lead to patient complications. Additionally, compromises are often made as to the size of the implant device when the implant device is used in the opposite compartment. Moreover, such an approach may not fully satisfy the anatomic requirements of the off design secondary application. For example, attempts to utilize an implant device in a manner in which the implant device is used in an opposite hand/compartment application can result in the use of an implant device that is smaller or larger than the implant device would have been if that implant device had been configured to anatomically fit that particular compartment and hand. Such compromises and/or the lack of anatomic conformance can provide less than ideal implanted conditions in each application.

Attempts to overcome such issues have included patient specific implants. Such implants can be based on information obtained from scans of the bone and/or knee structure of a patient. Moreover, such scanning can be utilized to generally match the tibial resection of the patient. Yet, in addition to being costly, such an approach further exposes the patient to additional medical scanning.

BRIEF SUMMARY

Embodiments of the present application provide unique implant devices. Further embodiments, forms, features, aspects, benefits, and advantages of the present application shall become apparent from the description and figures provided herewith.

An aspect of an embodiment of the present application is an implant device for implantation on a tibia that can include an outer edge including a first edge, a second edge, an anterior edge, and a posterior edge. At least a portion of the first and second edges can be separated by an ML width, and at least a portion of the anterior and posterior edges being separated by an AP width. Additionally, the outer edge can further include a posterior curve and an anterior curve, at least a portion of the anterior and posterior curves can extend along the second edge. Further, the anterior curve can have a radius of curvature that is about 75 to about 100 percent the ML width, the posterior curve can have a radius of curvature that is about 70 to about 90 percent the ML width, and the AP width can be about 160 percent to about 190 percent the M-L width.

Such an implant device can also include, among other features, one or more of the following, as well as various combinations thereof: the first edge being configured to be parallel to the midline AP axis of the tibia; the first edge being angled anterior to posterior to the AP axis of the tibia; the first edge having an angled orientation configured to follow the medial edge of the anterior and posterior cruciate ligaments; and/or the anterior and posterior curves being joined by a transition surface that is posterior of the midline of the AP axis of the tibia and which extends for a length that is about 0 to about 25 percent the ML width.

Another aspect of an embodiment of the present application is an implant device for implantation on a tibia that includes an outer edge having a first edge, a second edge, an anterior edge, and a posterior edge. At least a portion of the first and second edges can be separated by a ML width, and at least a portion of the anterior and posterior edges can be separated by an AP width. Further, the outer edge of the implant device can further include a posterior curve, a medial curve, and an anterior curve, at least a portion of the anterior, medial, and posterior curves extending along the second edge. Additionally, the anterior curve can have a radius of curvature that is about 75 to about 100 percent the ML width, and the anterior curve can extend about 60 to about 80 percent of ML width from the first edge. The media curve of the implant device can also have a radius of curvature that is about 90 to about 110 percent of the ML width, and a tangency of the medial curve to the AP axis of the tibia can be posterior the AP midline and up to 25 percent of the ML width. The posterior curve can have a radius of curvature that is about 70 to about 90 percent the ML width. Additionally, the posterior curve can begin about 0 to about 25 percent of the ML width from the first edge and extend to about 75 percent, but less than 100 percent, of the ML width from the first edge. Further, the AP width can be about 160 to about 190 percent the ML width.

Such an implant device can also include, among other features, one or more of the following, as well as various combinations thereof: the first edge being configured to be parallel to the midline AP axis of the tibia; the first edge being angled anterior to posterior to the AP axis of the tibia; and/or the first edge having an angled orientation configured to follow the medial edge of the anterior and posterior cruciate ligaments.

Another aspect of an embodiment of the present application is an implant device for implantation on a tibia that includes an outer edge having a first edge, a second edge, an anterior edge, and a posterior edge, at least a portion of the first and second edges can be separated by ML width, and at least a portion of the anterior and posterior edges can be separated by an AP width. The outer edge of the implant device can further include a lateral curve that extends along at least a portion of the second edge. The lateral edge can have a radius Of curvature that is about 55 to about 70 percent the ML width. Additionally, the lateral curve can begin within about 10 percent of the ML width from the first edge and the AP width can be about 110 to about 150 percent the ML width.

Such an implant device can also include, among other features, one or more of the following, as well as various combinations thereof: the first edge being configured to be parallel to the midline A-P axis of the tibia; the first edge being angled anterior to posterior to the A-P axis of the tibia; and/or the first edge having an angled orientation configured to follow the lateral edge of the anterior and posterior cruciate ligaments.

Another aspect of an embodiment of the present application is an implant device for implantation on a tibia that includes an outer edge having a first edge, a second edge, an anterior edge, and a posterior edge, at least a portion of the first and second edges can be separated by ML width, and at least a portion of the anterior and posterior edges can be separated by an AP width. Additionally, the outer edge of the implant device can further include a posterior curve, a lateral curve, and an anterior curve, at least a portion of the anterior, medial, and posterior curves extending along the second edge. The anterior curve can begin within about 20 percent of the ML width from the medial edge and extend to the lateral curve and can have a radius larger than the lateral curve up to and including an infinite radius. Additionally, the lateral curve can begin at a junction with the posterior curve, extend through the tangency with the second edge, and end at the junction of the anterior curve between about 30 to about 75 percent of the ML width from the first edge. The tangency of the lateral curve with the midline of the first edge can be within about 0 to about 20 percent of the ML width posterior of the midline. Further, the posterior curve can have a radius of curvature that is smaller than the radius of curvature of the anterior and lateral curves. The posterior curve can begin about 20 percent of the ML width from the first edge and extend to about 75 percent, but less than 100 percent, of the ML width from the first edge. Additionally, the AP width can be about 110 percent to about 150 percent the ML width.

Such an implant device can also include, among other features, one or more of the following, as well as various combinations thereof: the first edge being configured to be parallel to the midline AP axis of the tibia; the first edge being angled anterior to posterior to the AP axis of the tibia; and/or the first edge having an angled orientation configured to follow the lateral edge of the anterior and posterior cruciate ligaments.

Another aspect of an embodiment of the present application is an implant device for implantation on a tibia that includes an outer edge having a first edge, a second edge, an anterior edge, and a posterior edge, at least a portion of the first and second edges being separated by ML width, and at least a portion of the anterior and posterior edges being separated by an AP width. The outer edge can further include a posterior curve, two lateral curves, and an anterior curve, at least a portion of the anterior, lateral, and posterior curves extending along the second edge. The anterior curve can begin within about 20 percent of the ML width from the medial edge, extend to the lateral curve, and. have a radius larger than the lateral curve up to and including an infinite radius. The two lateral curves can begin at a junction with the posterior curve, extend through the tangency with the second edge, and end at the junction of the anterior curve between about 10 to about 60 percent of the ML width from the anterior edge. The two lateral curves can be composed of either one or two sections, the two lateral curves each having a radius that is larger than the radius of curvature of the posterior and anterior curves, and the tangency of the two lateral curves with the midline of the second edge being within about 0 to about 20 percent of the ML width posterior of the midline. The posterior curve can begin about 10 to about 60 percent of the ML width from the first edge. The posterior curve can be joined to the first edge by a relatively straight surface or a curve having a radius that exceeds the two lateral curves, and extend to about 75 percent, but less than 100 percent, of the ML width from the first edge. The AP width can be about 110 to about 150 percent the ML width.

Such an implant device can also include, among other features, one or more of the following, as well as various combinations thereof: the first edge can be configured to be parallel to the midline AP axis of the tibia; the first edge can be angled anterior to posterior to the AP axis of the tibia; and/or the first edge can have an angled orientation configured to follow the lateral edge of the anterior and posterior cruciate ligaments.

Another aspect of an embodiment of the present application is an implant device for implantation on a tibia that includes an outer edge having a first edge, a second edge, an anterior edge, and a posterior edge, at least a portion of the first and second edges being separated by ML width, and at least a portion of the anterior and posterior edges being separated by an AP width. An end of the first edge can be angled anterior to posterior to the AP axis of the tibia to provide an end of the first edge adjacent to the posterior edge at a posterior offset position. The outer edge can further include a posterior curve, a lateral curve, and an anterior curve, at least a portion of the anterior, lateral, and posterior curves can extend along the second edge. The anterior curve can begin within about 20 percent of the ML width from the first edge, extends to the lateral curve, and have a radius that is larger than the lateral curve up to and including an infinite radius. The lateral curve can begin at a junction with the posterior curve, extend through the tangency with the second edge, and end at the junction of the anterior curve between about 40 to about 100 percent of the ML width from the first edge. The radius of curvature of the lateral curve can be smaller than the radii of curvature of the anterior and posterior curves. The tangency of the lateral curve with the midline of the first edge can be within about 0 to about 20 percent of the ML width posterior of the midline. The posterior curve can have a radius of curvature that is smaller than the radius of curvature of the anterior curve and larger than the lateral curve. The posterior curve can extend to about 70 to about 100 percent of the ML width from the first edge, and the AP width can be about 110 to about 150 percent the ML width. The first edge of such an implant device can also have an angled orientation that is configured to follow the lateral edge of the anterior and posterior cruciate ligaments.

Another aspect of an embodiment of the present application is an implant device for implantation on a tibia that includes an outer edge having a first edge, a second edge, an anterior edge, and a posterior edge. At least a portion of the first and second edges can be separated by a ML width, and at least a. portion of the anterior and posterior edges can be separated by an AP width. The outer edge can further include a posterior curve, a lateral curve, and an anterior curve, at least a portion of the anterior, lateral, and posterior curves can extend along the second edge. The anterior curve can begin within about 20 percent of the ML width from the medial edge, extend to the lateral curve, and have a radius that is larger than the lateral curve, up to and including an infinite radius. The lateral curve can begin at a junction with the posterior curve, extend through the tangency with the second edge, and end at the junction of the anterior curve between about 40 to about 60 percent of the ML width from the first edge. The tangency of the lateral curve with the midline of the first edge can be within about 0 to about 20 percent of the ML width posterior of the midline. The posterior curve can have a radius of curvature that is smaller than the radius of curvature of the anterior and lateral curves. The posterior curve can begin about 20 percent of the ML width from the first edge and extend to about 40 to about 60 percent of the ML width from the first edge. The radius of curvature of the posterior curve can be smaller than the radii of curvature of the anterior and lateral curves. Additionally, the AP width can be about 110 percent to about 150 percent the ML width.

Such an implant device can also include, among other features, one or more of the following, as well as various combinations thereof: first edge can be configured to be parallel to the midline AP axis of the tibia; the first edge can be angled anterior to posterior to the AP axis of the tibia, or the first edge can have an angled orientation that is configured to follow the lateral edge of the anterior and posterior cruciate ligaments.

Another aspect of an embodiment of the present application is an implant device for implantation on a tibia having an outer edge that includes a first edge, a second edge, an anterior edge, and a posterior edge, at least a portion of the first and second edges being separated by ML width, and at least a portion of the anterior and posterior edges being separated by an AP width. The outer edge further includes a posterior curve, two lateral curves, and an anterior curve, at least a portion of the anterior, lateral, and posterior curves extending along the second edge. The anterior curve begins within about 20 percent of the ML width from the medial edge, extends to one of the two lateral curves, and has a radius larger than the lateral curve up to and including an infinite radius. The anterior curve can be coupled to the first edge by a portion of the anterior edge that is acute or at a right angle to the first edge. The two lateral curves can begin at a junction with the posterior curve, extend through the tangency with the second edge of the first edge, and end at the junction of the anterior curve between about 20 to about 50 percent of the ML width from the anterior edge. The tangency of the two lateral curves with the midline of the second edge can be within about 0 to about 20 percent of the ML width posterior of the midline. The posterior curve can begin extending from about the first edge to a distance about 20 percent of the ML width from the first edge. The posterior curve can have a radius that is smaller than the radii of curvature of the two lateral curves, and the AP width can be about 110 percent to about 150 percent the ML width.

Such an implant device can also include, among other features, one or more of the following, as well as various combinations thereof: the first edge being configured to be parallel to the midline AP axis of the tibia; the first edge being angled anterior to posterior to the AP axis of the tibia; and/or the first edge having an angled orientation that is configured to follow the lateral edge of the anterior and posterior cruciate ligaments.

Another aspect of an embodiment of the present application is an implant device for implantation on a tibia that includes an outer edge having a first edge, a second edge, an anterior edge, and a posterior edge, at least a portion of the first and second edges being separated by ML width, and at least a portion of the anterior and posterior edges being separated by an AP width. An end of the first edge can be angled anterior to posterior to the AP axis of the tibia to provide an end of the first edge adjacent to the posterior edge at a posterior offset position. The outer edge can further include a posterior curve, a lateral curve, and an anterior curve, at least a portion of the anterior, lateral, and posterior curves can extend along the second edge. The anterior curve can begin within about 20 percent of the ML width from the medial edge, extend to the lateral curve, and have a radius that is larger than the lateral curve. The lateral curve can begin at a junction with the posterior curve, extend through the tangency with the second edge, and end at the junction of the anterior curve between about 40 to about 60 percent of the ML width from the first edge. The tangency of the lateral curve with the midline of the first edge can be within about 0 to about 20 percent of the ML width posterior of the midline. The posterior curve can have a radius of curvature that is smaller than the radius of curvature of the anterior and lateral curves. The posterior curve can begin about 25 to about 35 percent of the ML width from the offset end of the first edge. The posterior curve and first end can be joined by a transition surface that is angled in the posterior direction. The radius of curvature of the posterior curve can be smaller than the radii of curvature of the anterior and lateral curves, and the AP width can be about 110 percent to about 150 percent the ML width. The first edge of such an implant device can also have an angled orientation that is configured to follow the lateral edge of the anterior and posterior cruciate ligaments.

BRIEF DESCRIPTION OF THE DRAWINGS

The description herein makes reference to the accompanying figures wherein like reference numerals refer to like parts throughout the several views.

Figure 1:
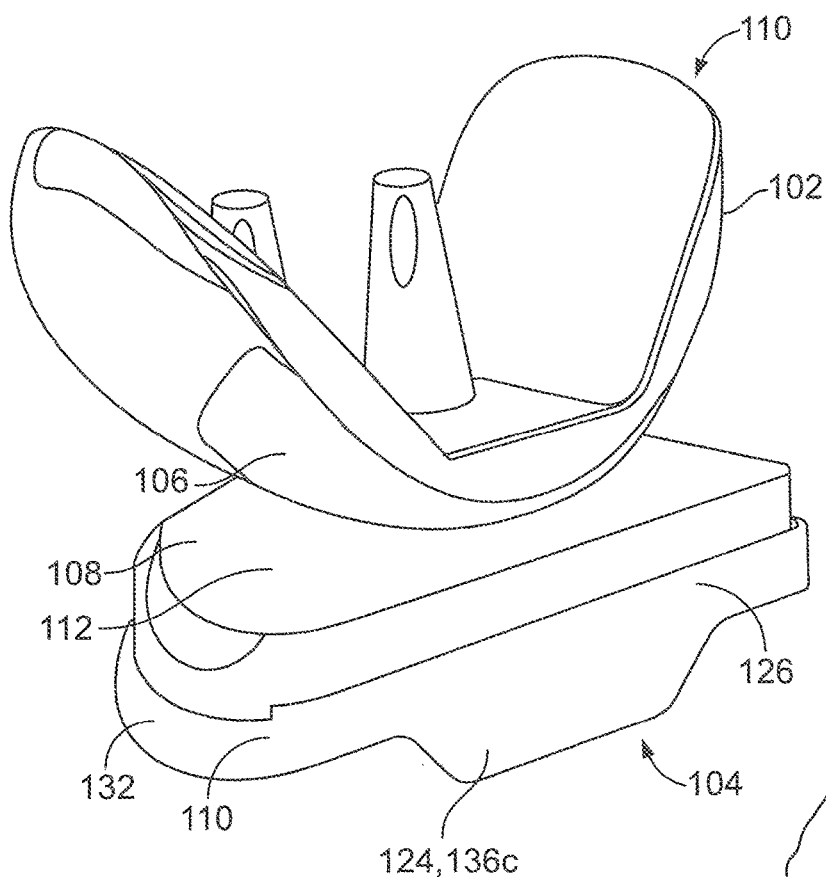
FIG. 1 illustrates a side perspective view of an exemplary implant device that can be utilized for unicompartmental knee replacement.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities. shown in the attached drawings. Further, like numbers in the respective figures indicate like or comparable parts.

DESCRIPTION OF THE ILLUSTRATED EMBODIMENTS

Certain terminology is used in the foregoing description for convenience and is not intended to be limiting. Words such as "upper," "lower," "top," "bottom," "first," and "second" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof. As used herein, the terms "about" and "substantially" may be applied to modify any quantitative representation that could permissibly vary without resulting in a change in the basic function to which it is related.

FIG. 1 illustrates a side perspective view of an exemplary implant 100 that can be utilized for unicompartmental knee replacement. According to certain embodiments, the exemplary implant 100 can include a femoral component 102 and a tibial component 104. An upper portion of the tibial component 104 has tibial articular surface 108 which contacts or articulates against a femoral articular surface 106 of the femoral component 102 in a manner that at least assists in providing a functioning knee joint. According to certain embodiments, the tibial component 104 can include a tibial baseplate 110 and an insert 112, the insert 112 being configured to provide the tibial articular surface 106. Further, according to certain embodiments, the tibial baseplate 110 and insert 112 may be separate components that are constructed from different material. Further, the insert 112 can include one or more trial inserts that is/are used at least temporarily during the implantation procedure or surgery, as well as inserts that are selected for final implantation with the implant 100.

Figure 2:
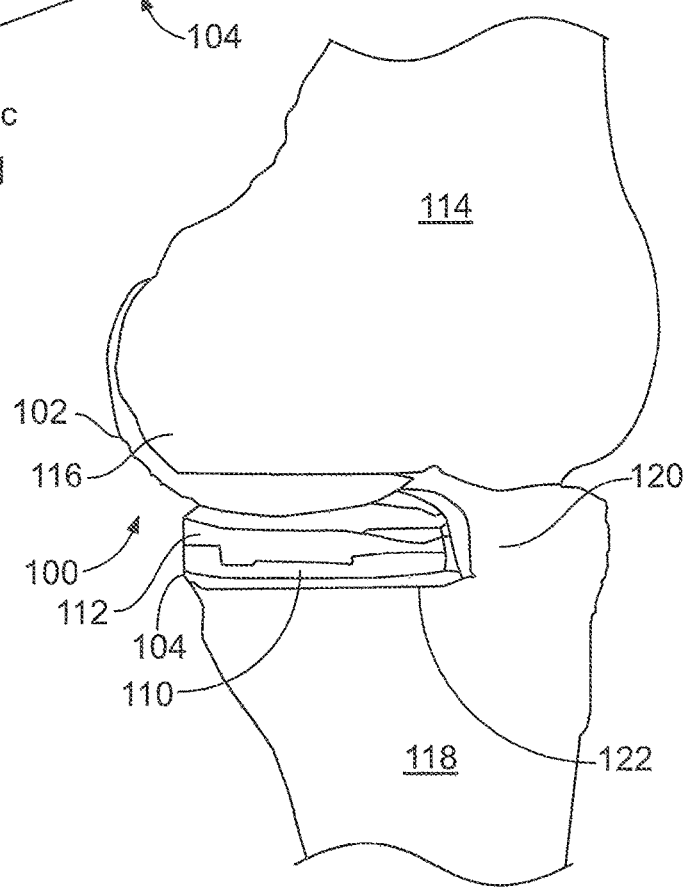
FIG. 2 illustrates a side view of the exemplary implant device depicted in FIG. 1 implanted in a knee joint.
Figure 3:
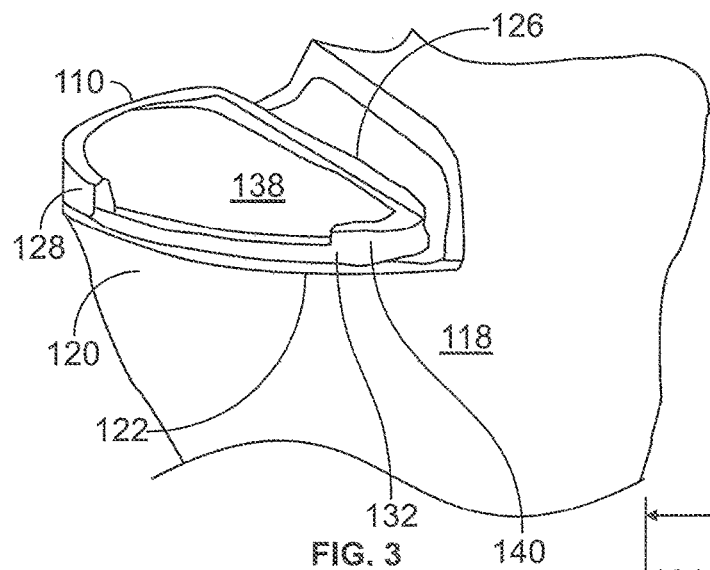
FIG. 3 illustrates a perspective view of an exemplary tibial baseplate mounted in a resected tibial plateau of a tibia.

Referencing FIG. 2, the femoral component 102 can be configured to be operably mounted or otherwise secured to the distal femur portion 116 of the femur 114, while the tibial component 104 can be configured to be operably mounted or otherwise secured to the proximal tibia portion 120 of the tibia 118. Further, as illustrated in FIG. 3, according to certain embodiments, the tibial component 104 can be secured in a resected tibial plateau 122 of a tibia 118 that can be provided by shaping, and/or otherwise by removal of a portion of, the tibia 118 such as, for example, removing a portion of, or shaping, the right or left lateral or medial portions or compartments of the proximal tibia portion 120 of the tibia 118. Further, the tibial baseplate 110 can include one or fixation members 124 that can at least assist in the tibial baseplate 110 being secured to the tibia. A variety of types of fixation members 124, or combinations of fixation members 124, can be utilized for securing the tibial baseplate 110 to the tibia portion 120. For example, the fixation member(s) 124 can include, or be configured for use with, mechanical fasteners, and/or have other characteristics that facilitate the tibial baseplate 110 being secured via use of an adhesive such as, for example, cement. Such fixation members 124 include, but are not limited to, one or more screws, pegs, posts, fins, rails, cavities, and/or a combination thereof. At least certain types of fixation members 124 can be configured to provide features or a geometry to the tibia baseplate 110 that can, at least when compared to relatively flat surfaces, assist in enhancing implant to cement, and/or cement to bone, fixation.

Figure 4:
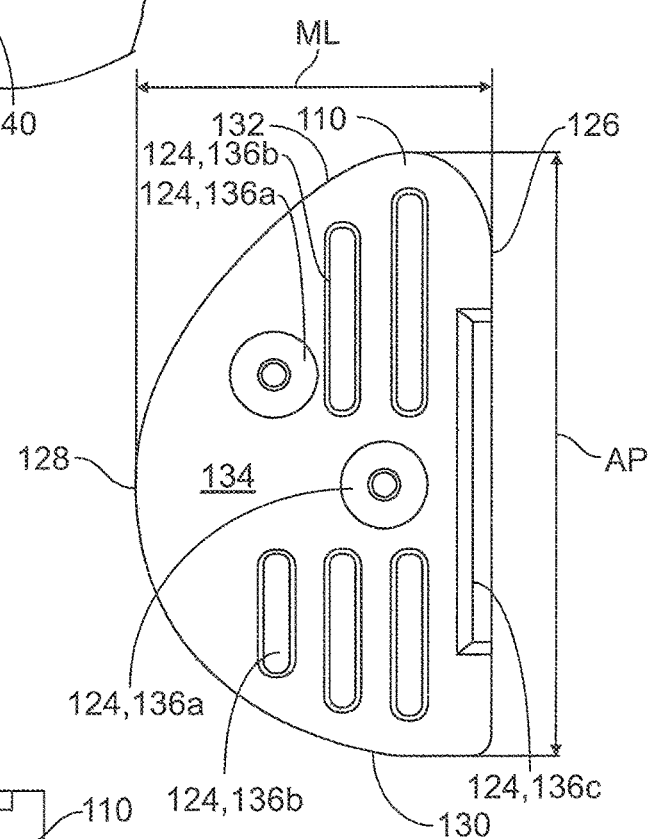
FIG. 4 illustrates a distal side view of an exemplary tibial baseplate.
Figure 5:
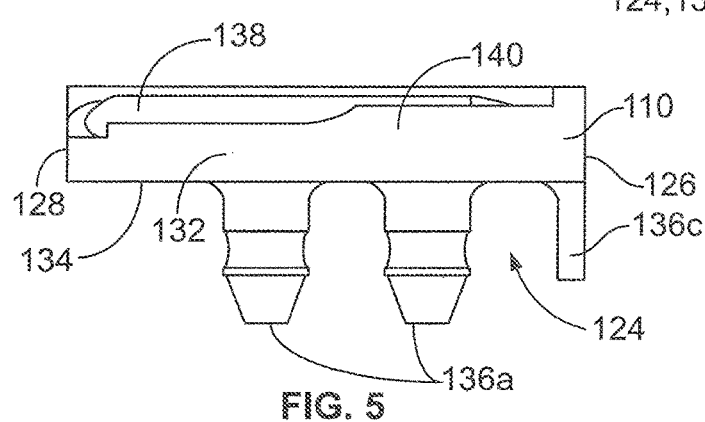
FIG. 5 illustrates a front side view of the exemplary tibial baseplate depicted in FIG. 4.

FIGS. 4 and 5 illustrate distal and front side views, respectively, of an exemplary tibial baseplate 110. The tibial baseplate 110 includes a first edge 126 and a second edge 128 at opposing sides of the tibial baseplate 110, the first edge 126 being configured for placement at a location that is closer to a center or mid-point location of tibia than the second edge 128, and moreover, the second edge 128 being in closer proximity to the outer side region of the tibia than the first edge 126. Further, medial and lateral edges of the baseplate 110, which, depending on orientation, can generally be provided by first and second edges 126, 128 of the baseplate 110, can be generally separated from each other by a medial-lateral (ML) width, as shown, as shown in FIG. 4. The tibial baseplate 110 also includes an anterior side 132 and a posterior side 130 at opposing sides of the tibial baseplate 110, and which are separated by an anterior-posterior (AP) length, which is also shown in FIG. 4. The distal side 134 of the tibial baseplate 110 can be configured to be positioned in a direction or orientation in which the distal side 134 faces towards an adjacent portion of the tibia 118 such as, for example, a resected portion of the lateral or medial compartments of the proximal tibia portion 120. Further, the distal side 134 of the tibial baseplate 110 may include features that can assist in the tibial baseplate 110 being secured to the tibia 118 such as, for example, fixation members 124 including, for example, pegs 136a, cavities 136b, a fin 136c, and/or combinations thereof, among other types of fixed members 124.

A proximal side 138 of the tibial baseplate 110 can be configured to abut and/or receive insertion of the insert 112. Further, according to certain embodiments, the proximal side 138 of the tibial baseplate 110 can include one or more features that can at least assist in retaining an engagement with between the tibial baseplate 110 and the insert 112 including, for example, a lip 140 about at least a portion of the tibial baseplate 110, among other features.

Figure 6A:
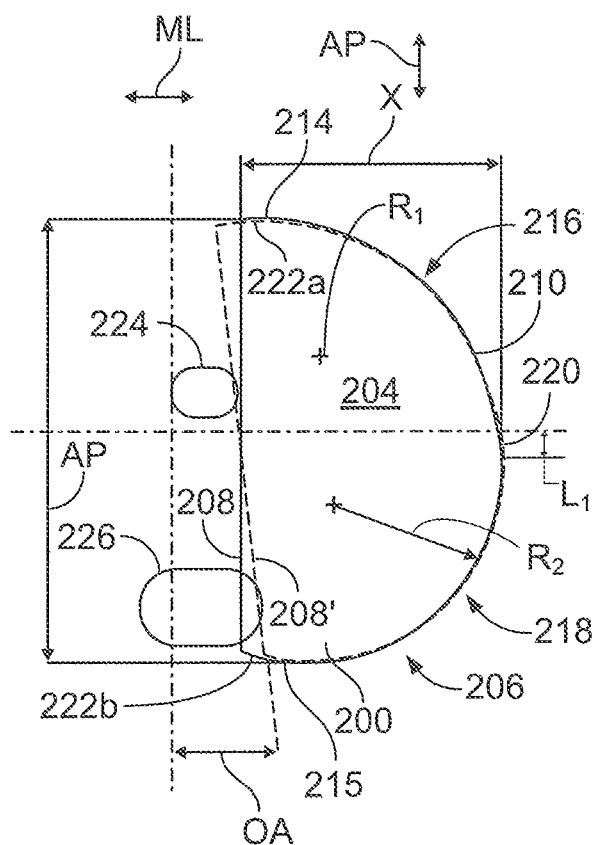
FIG. 6A illustrates a proximal side view of a medial unicondylar tibia implant having at least two curves according to certain embodiments of the present application.
Figure 6B:
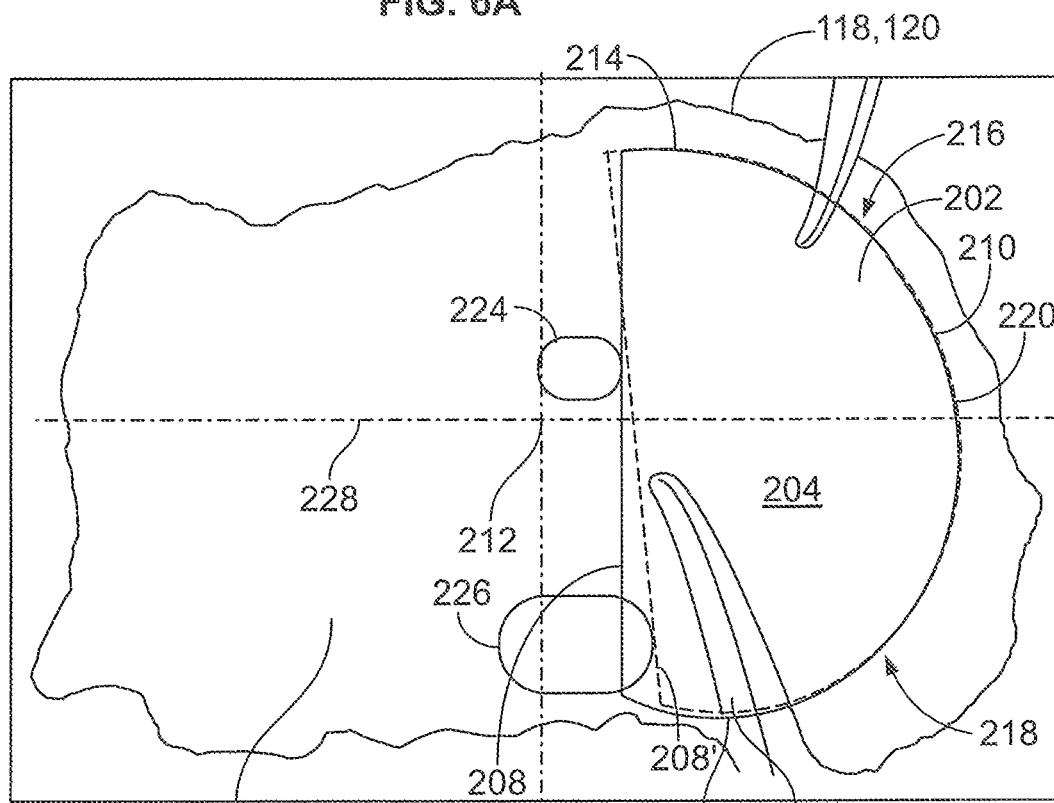
FIG. 6B illustrates the medial unicondylar tibia implant(s) depicted in FIG. 6A and certain identified geometries of the implant(s) superimposed over an exemplary proximal tibia portion of a tibia.

FIG. 6A illustrates a proximal side view of a medial unicondylar tibia implant device 200 having at least two curves according to certain embodiments of the present application. Further, FIG. 6B illustrates the medial unicondylar tibia implant device 200 and certain identified geometries of the implant device 200 depicted in FIG. 6A superimposed over an exemplary proximal tibia portion of a tibia 118. While FIGS. 6A and 6B illustrate a medial unicondylar tibia implant device 200 for a medial compartment 202 of a tibia 118 for the left knee, similar features also may be utilized for a medial compartment of a tibia of the right knee, wherein the location or orientation of the depicted medial unicondylar tibia implant device 200 may be adjusted to accommodate the change in hand from left to right.

According to certain embodiments, the proximal side 204 of the tibia implant device 200 depicted in FIGS. 6A and 6B, which can be the side of the tibia implant device 200 facing away from the tibia portion 120, can have a geometry that is configured to provide either an, articulating surface such as, for example, cartilage and meniscal substituting, or to receive or be coupled to a secondary device that can provide such an articulating feature and/or articulating surface. For example, according to certain embodiments, the portion of the tibia implant device 200 shown in FIGS. 6A and 6B, as well as the implant devices 300-1000 discussed below with respect to FIGS. 7A-14B, can generally correspond to a profile or shape of at least certain aspects of at least the proximal side 204 of one or both of a tibial baseplate and/or an insert of a tibial component of a knee implant. Further, the configurations and features of the implant devices 200-1000 discussed herein provide benefits in improvements in at least the anatomical size, shape, and/or configuration provided by the implant device 200-1000 between the bone facing side, or first edge of the implant device 200-1000 and the away from bone facing edge, such as the second edge, of the implant device 200-1000.

The implant device 200 shown in FIGS. 6A and 6B includes an outer edge 206 that includes a first edge 208, 208' and a second edge 210 at opposing sides of the implant device 200. While the first edge 208, 208' is depicted in FIGS. 6A and 6B as being a relatively straightedge, the first edge 208, 208' can have a variety of other configurations such as, for example, configurations that generally follow or otherwise provide clearance from the soft tissue boundaries of the tibial spine. For example, according to certain embodiments, the first edge 208, 208' can be straight, curved, and/or scalloped, as well as various combinations thereof; among other shapes and configurations. As discussed below in more detail, according to certain embodiments, the first edge 208 of the implant device 200 may be generally parallel to the tibia spine or AP tibia axis 212 of the tibia 118, while, according to other embodiments, the first edge 208' of the implant device 200 can be non-parallel to the tibia spine or AP tibia axis 212. Further, the first edge 208, 208' of the implant device 200 can be configured for placement at a location that is closer to a center or mid-point location of tibia 118 than the second edge 210, and thus the second edge 210 is configuration for positioning at a location in closer proximity than the first edge 208, 208' to the outer side of the tibia 118. In the depicted embodiment, the first edge 208, 208' and second edge 210 can be configured to provide the implant device 200 with a ML width in the ML direction (as indicated by the "ML" direction in FIG. 6A) that, for purposes of discussion, is identified in FIG. 6A as "X". The ML width can, according to certain embodiments, represent the maximum ML width of the implant device 200 in the ML direction.

Additionally, the outer edge 206 of the implant device 200 also can include an anterior edge 214 and a posterior edge 215. According to certain embodiments, the anterior and posterior edges 214, 215 generally extend between the first and second edges 208, 208', 210 along opposing sides of the outer edge 206 of the implant device 200. According to the illustrated embodiment, the anterior edge 214 and a posterior edge 216 can be separated from each other by an AP width in the AP direction (as indicated by the "AP" direction in FIG. 6A). The AP width can, according to certain embodiments, correspond to the maximum width of the implant device 200 in the AP direction. According to the illustrated embodiment, the aspect ratio of the AP width to the ML width of the implant device 200 can be about 1.7:1, among other ratios, as illustrated, for example, generally by the "AP" width depicted in FIG. 6A.

According to the embodiment depicted in FIGS. 6A and 6B, the medial unicondylar tibia implant device 200 has at least two medial curves, which, in the illustrated example, includes an anterior curve 216 and a posterior curve 218. The anterior and posterior curves 216, 218 can generally extend along at least the second edge 210 of the implant device 200. The second edge 210 also may include a transition surface 220 that joins the anterior and posterior curves 216, 218 along the second edge 210. The transition surface 220 can have a variety of different shapes or configurations including, for example, being a relatively flat, straight, or angled surface, among other shapes. Further, the transition surface 220 can have a variety of lengths between the anterior and posterior curves 216, 218. For example, according to the illustrated embodiment, the transition surface 220 can be a generally straight edge that extends between the anterior and posterior curves 216, 218 at a length in the AP direction (as generally indicated by "L.sub.1" in FIG. 6A), the ratio of the length of the transition surface 220 to the ML width of the implant device 200 being, for example, about 0.1:1.

Further, according to certain embodiments, the posterior curve 218 also can extend along at least a portion of the posterior edge 215 of the implant device 200. Further, according to certain embodiments, the posterior curve 218 also can extend along at least a portion of the posterior edge 215. The extent that the posterior curve 218 extends along the posterior edge 215 can vary. For example, according to certain embodiments, the posterior edge 215 can include a transition surface having a shape or orientation that is different than the curvature of the posterior curve 218, and which adjoins the portion of the posterior curve 218 that extends along the posterior edge 215 to the first edge 208, 208'. Alternatively, the according to certain embodiments, the posterior curve 218 can extend along the posterior edge 215 until generally reaching the first edge 208, 208'.

Similar to the posterior edge 215, the anterior curve 216 also can extend along at least a portion of the anterior edge 214 of the implant device 200. Further, according to certain embodiments, the anterior curve 216 also can extend along at least a portion of the anterior edge 214. The extent that the anterior curve 216 extends along the anterior edge 214 can vary. For example, according to certain embodiments, the anterior edge 214 can include a transition surface having a shape or orientation that is different than the curvature of the anterior curve 216, and which adjoins the portion of the anterior curve 216 that extends along the anterior edge 214 to the first edge 208, 208'. Alternatively, according to certain embodiments, the anterior curve 216 can extend along the anterior edge 214 until generally reaching the first edge 208, 208'.

The anterior and posterior curves 216, 218 can have a variety of sizes. Further, the radius of curvature of the anterior and posterior curves 216, 218 can be similar or dissimilar. For example, according to certain embodiments, the anterior curve 216 can have radius (as indicated by the radius of curvature "R.sub.1" in FIG. 6A) that is approximately 75 to 100 percent of the ML dimension, and thus provides a ratio of radius of curvature for the anterior curve 216 to the ML width of from about 0.75:1 to about 1:1, among other ratios. Moreover, according to certain embodiments, the radius of curvature for the anterior curve 216 can be 70 to 90 percent, and more specifically, 90 percent, the ML width. Additionally, for example, the posterior curve 218 can have radius (as indicated in FIG. 6A by "R.sub.2") that is approximately 70 to 90 percent of the ML dimension, and thus provides a ratio of radius of curvature for the posterior curve 218 to the ML width of from about 0.7:1 to about 0.9:1, and more specifically, about 0.8:1 the ML width, among other ratios.

As shown in FIGS. 6A and 6B, according to certain embodiments, the first edge 208 of the implant device 200 can extend in a direction that is generally parallel to the tibia spine or AP tibia axis 212 (FIG. 6B). Conversely, according to other embodiments, the first edge 208 of the implant device 200 is not parallel to the tibia spine or AP tibia axis 212. For example, the first edge 208' of the implant device 200 can be offset (as indicated by offset angle "OA" in FIG. 6A) by about 1 degree to about 20 degree, and more specifically, about 3 degrees to about 8 degrees, among other degrees of offset, relative to the first edge 208 of an implant device 200 that is generally parallel to the tibia spine or AP tibia axis 212. Further, FIGS. 6A and 6B illustrate an orientation of the first edge 208' that can be angled anterior to posterior of the AP tibia axis 212 and generally follow the medial edge of the anterior cruciate ligament 224 (ACL) and posterior cruciate ligament 226 (PCL) relative to a location at which the ACL 224 and PCL 226 would be attached to the tibia 118. Additionally, according to such a configuration in which the first edge 208' is non-parallel, or angularly offset relative, to the tibia spine or AP tibia axis 212, the aspect ratio of the AP width to the ML width of the implant device 200 can be less than about 1.45:1, among other ratios.

Additionally, according to certain embodiments the ratio of the radius of curvature of the anterior curve 216 to the ML width can be approximately 0.75:1 to approximately 1:1, the ratio of the radius of curvature of the posterior curve 218 to the ML width can be approximately 0.7:1 to approximately 0.9:1, and the aspect ratio of the AP width to the ML width can be approximately 1.6:1 to approximately 1.9:1, among other ratios. Additionally, according to certain embodiments, the anterior and posterior edges 214, 215 can each include a curve transition surface 222a, 222b in which the anterior and posterior curves 216, 218, respectively, terminate parallel to the AP midline 228 of the tibia 118 at a location that is posterior of the AP midline 228 and extend along a length of, for example, up to 0.25 percent of the ML width. The outer edge 206 also can include other transition surfaces or curves including, for example, edge blends at locations along the outer edge 206 where otherwise non-tangent edges may occur.

Figure 7A:
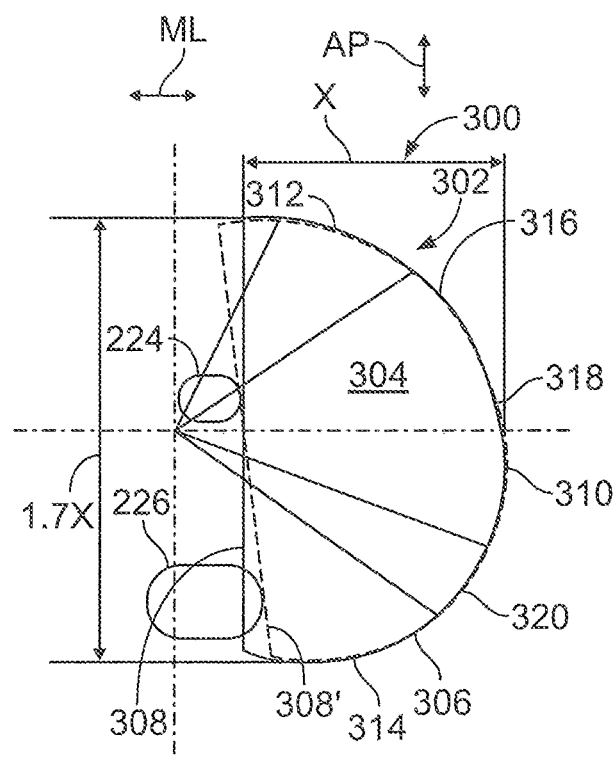
FIG. 7A illustrates a proximal side view of a medial unicondylar tibia implant having at least three curves according to certain embodiments of the present application.
Figure 7B:
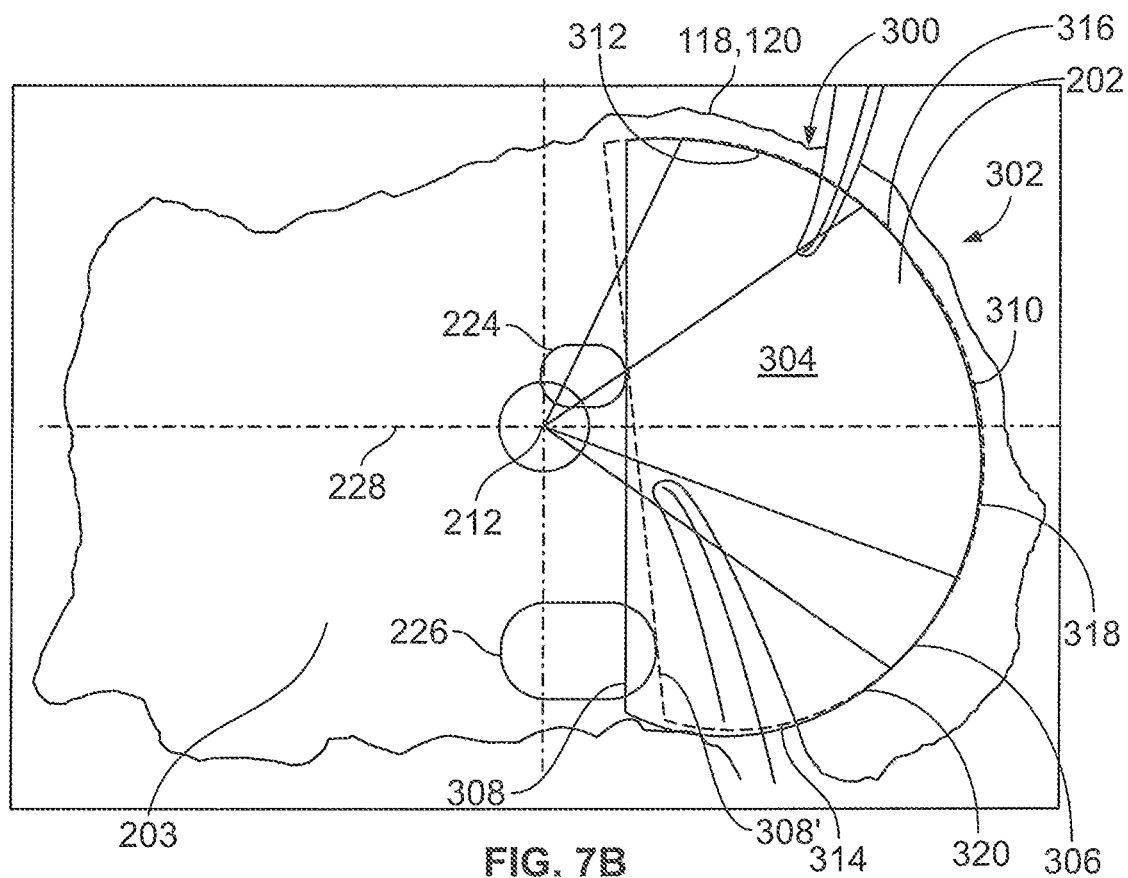
FIG. 7B illustrates the medial unicondylar tibia implant(s) depicted in FIG. 7A and certain identified geometries of the implant(s) superimposed over an exemplary proximal tibia portion of a tibia.

FIG. 7A illustrates a proximal side view of a medial unicondylar tibia implant device 300 having at least three medial curves 302 according to certain embodiments of the present application. Further, FIG. 7B illustrates the medial unicondylar tibia implant device 300 and certain identified geometries of the implant devices 300 depicted in FIG. 7A superimposed over an exemplary proximal tibia portion of a tibia 118. While FIGS. 7A and 7B illustrate a medial unicondylar tibia implant devices 300 for a medial compartment 202 of a tibia 118 for the left knee, similar features also may be utilized for a medial compartment of a tibia for the right knee, wherein the location or orientation of the depicted medial unicondylar tibia implant device 300 may be adjusted to accommodate the change in hand from left to right.

According to certain embodiments, the proximal side 304 of the tibia implant device 300 depicted in FIGS. 7A and 7B can be face away from the tibia portion 120. Further, the proximal side 304 of the tibia implant device 300 can have a geometry that is configured to provide either an articulating surface such as, for example, cartilage and meniscal substituting, or to receive or be coupled to a secondary device that can provide such an articulating feature and/or articulating surface. For example, according to certain embodiments, the portion of the tibia implant device 300 shown in FIGS. 7A and 7B, can generally correspond to a profile or shape of at least certain aspects of the proximal side 304 of one or both of a tibial baseplate and/or an insert of a tibial component of a knee implant. Further, according to certain embodiments, the implant 300 can have an edge that follows the medial edge of the ACL 224 and PCL 226, as discussed below.

The implant device 300 shown in FIGS. 7A and 7B includes an outer edge 306 having a first edge 308, 308' and a second edge 310 at opposing sides of the implant device 300. While the first edge 308, 308' is depicted in FIGS. 7A and 7B as being a relatively straight edge, the first edge 308, 308' can have a variety of other configurations such as, for example, configurations that generally follow or otherwise provide clearance from the soft tissue boundaries of the tibial spine. For example, according to certain embodiments, the first edge 308, 308' can be straight, curved, and/or scalloped, as well as various combinations thereof, among other shapes and configurations. Similar to the first edges 208, 208' of the implant device 200 discussed above with respect to FIGS. 6A and 6B, according to certain embodiments, the implant device 300 depicted in FIGS. 7A and 7B can be configured for the first edge 308, 308' to be generally parallel or non-parallel to the tibia spine or AP tibia axis 212 of the tibia 118. Alternatively, according to certain embodiments, the first edge 308' of the implant device 300 depicted in FIGS. 7A and 7B can be angled anterior to posterior of the AP tibia axis 212 in a manner similar to that discussed above with respect to an embodiment of the implant device 200 shown in FIGS. 6A and 6B. Further, in the depicted embodiment, the first edge 308, 308' and second edge 310 can be configured to provide the implant device 300 with a ML width in the ML direction (as indicated by the "ML" direction in FIG. 7A) that, for purposes of discussion, is identified in FIG. 7A as "X". The ML width can, according to certain embodiments, represent the maximum ML width of the implant device 300 in the ML direction.

Additionally, the outer edge 306 of the implant device 300 also can include an anterior edge 312 and a posterior edge 314. According to certain embodiments, the anterior and posterior edges 312, 314 generally extend between the first and second sides 308, 308', 310 along opposing sides of the outer edge 306 of the implant device 300. According to the illustrated embodiment, the anterior edge 312 and a posterior edge 314 can be separated from each other by an AP width in the AP direction (as indicated by the "AP" direction in FIG. 7A). The AP width can, according to certain embodiments, correspond to the maximum width of the implant device 300 in the AP direction. According to the embodiments shown in FIGS. 7A and 7B, the aspect ratio of the AP width to the ML width of the implant device 300 can be about 1.6:1 to about 1.9:1, among other ratios.

According to the embodiment depicted in FIGS. 7A and 7B, the medial unicondylar tibia implant device 300 has at least three medial curves 302, which, in the illustrated embodiment, includes an anterior curve 316, a medial curve 318, and a posterior curve 320. The anterior curve 316 can begin along at least a portion of the anterior edge 312 and extend along the second edge 310 until being at a linear distance from the first edge 308, 308' that is approximately 60 percent to approximately 80 percent the ML width. Further, according to certain embodiments, the radius of curvature of the anterior curve 316 is approximately 75 percent to approximately 100 percent the ML width. The medial curve 318 is positioned between the anterior and posterior curves 316, 320, and has a radius of curvature that is approximately 90 to approximately 110 percent of the ML width. Additionally, the tangency of the medial curve 318 to the AP tibia axis 212 of the tibia 118 is posterior the AP midline 228, and up to about 25 percent of the ML dimension. The posterior curve 320 has a curvature radius that can be approximately 70 percent to approximately 90 percent of the ML width of the implant device 300. Further, the posterior curve 320 can extend from a linear distance of about 0 percent to about 25 percent of the ML width from the first edge 308, 308' along the posterior edge 314 to a linear distance of about 75 percent to less than 100 percent of the ML width from the first edge 308, 308'. The outer edge 306 also can include other transition surfaces or curves including, for example, edge blends at locations along the outer edge 306 where non-tangent edges may otherwise occur.

Figure 8A:
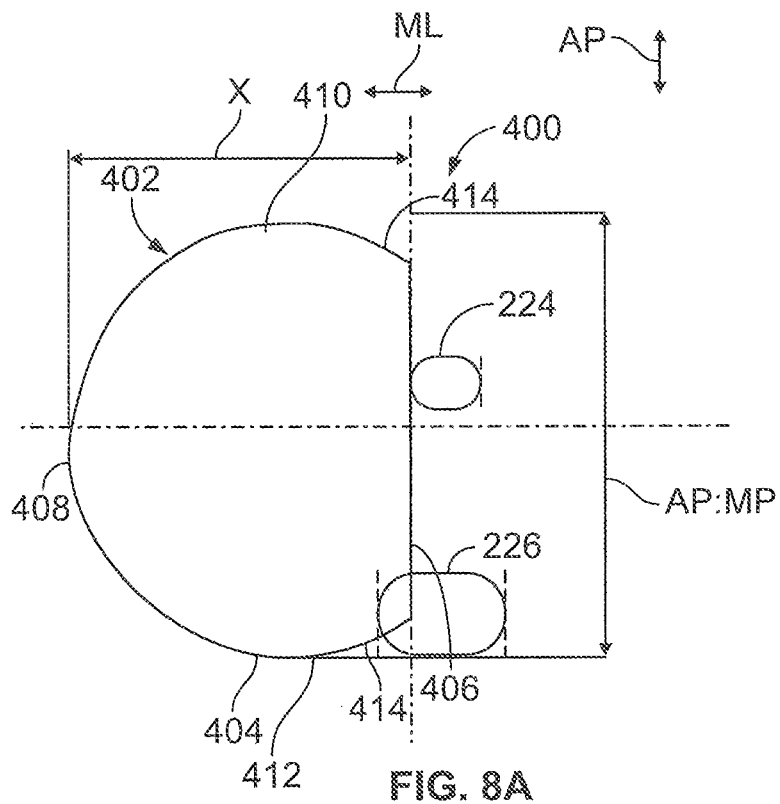
FIG. 8A illustrates a proximal side view of a lateral unicondylar tibia implant having at least one lateral curve according to certain embodiments of the present application.
Figure 8B:
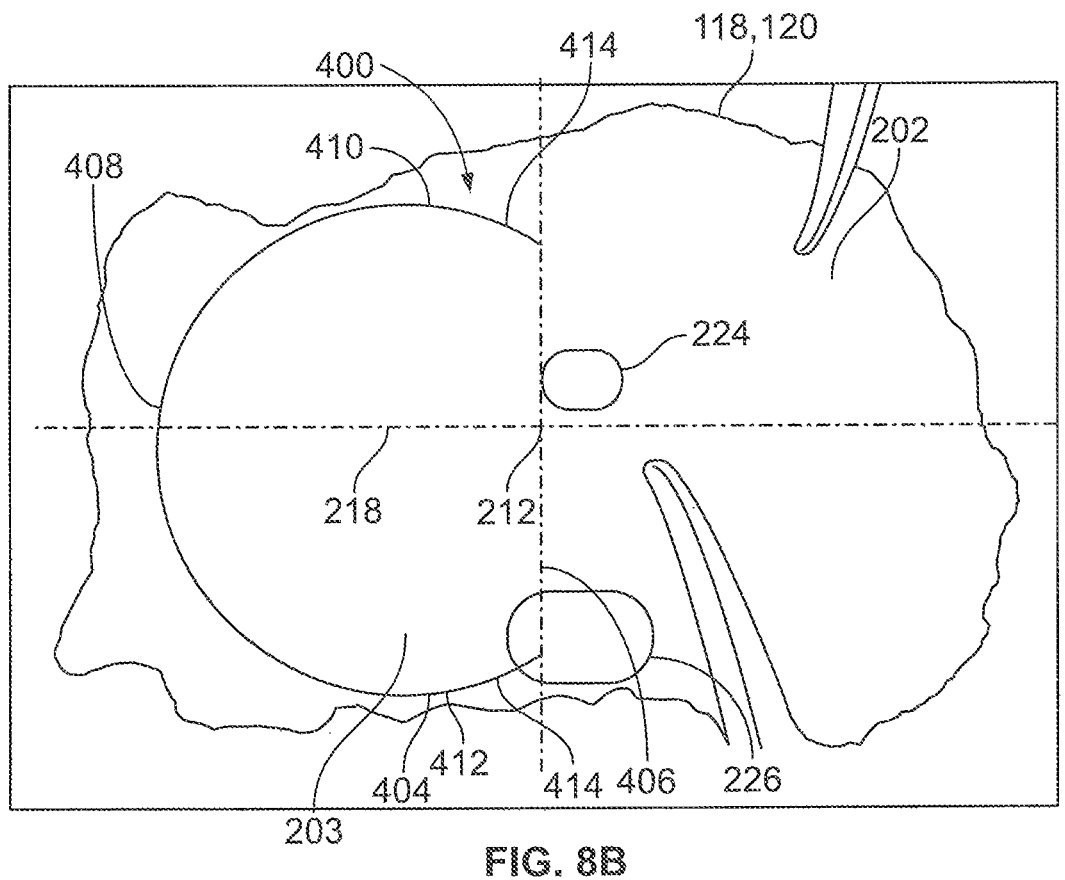
FIG. 8B illustrates the lateral unicondylar tibia implant(s) depicted in FIG. 8A and certain identified geometries of the implant(s) superimposed over an exemplary proximal tibia portion of a tibia.

FIG. 8A illustrates a proximal side view of an embodiment of a lateral unicondylar tibia implant device 400 having at least one lateral curve 402 according to certain embodiments of the present application. Further, FIG. 8B illustrates the lateral unicondylar tibia implant device 400 depicted in FIG. 8A superimposed over an exemplary proximal tibia portion of a tibia 118. While FIGS. 8A and 8B illustrate a lateral unicondylar tibia implant device 400 for a lateral compartment 203 of a tibia 118 for the left knee, similar features also may be utilized for a lateral compartment of a tibia for the right knee, wherein the location or orientation of the depicted lateral unicondylar tibia implant device 400 can be adjusted to accommodate the change in hand from left to right.

The implant device 400 shown in FIGS. 8A and 8B includes an outer edge 404 having a first edge 406 and a second edge 408 at opposing sides of the implant device 400. While the first edge 406 is depicted in FIGS. 8A and 8B as being a relatively straight edge, the first edge 406 can have a variety of other configurations such as, for example, configurations that generally follow or otherwise provide clearance from the soft tissue boundaries of the tibial spine. For example, according to certain embodiments, the first edge 406 can be straight, curved, and/or scalloped, as well as various combinations thereof, among other shapes and configurations. Further, as shown in FIG. 8A, the first edge 406 is closer to the center of the tibia 118 than the second edge 408, and thus the first edge 406 can be considered bone facing. According to certain embodiments, the first edge 406 can be configured to be generally parallel to the tibia spine or AP tibia axis 212 of the tibia 118. However, alternatively, according to certain embodiments, the first edge of the implant device 400 can be angled anterior to posterior relative to the AP tibia axis 212 in a manner that may facilitate the first edge 406 following a lateral edge of the ACL 224 and PCL 226. Further, as with other portions of the outer edge 404 and other implant devices discussed herein, transition surfaces, including curves, edge blends, and/or straight lines, as well as a combination thereof, also can be present where non-tangent edges may otherwise occur.

Additionally, in the depicted embodiment, the first edge 406 and the second edge 408 may be configured to provide the implant device 400 with a ML width in the ML direction (as indicated by the "ML" direction in FIG. 8A) that, for purposes of discussion, is identified in FIG. 8A as a length of "X". The ML width can, according to certain embodiments, represent the maximum ML width of the implant device 400 in the ML direction.

The outer edge 404 of the implant device 400 also can include an anterior edge 410 and a posterior edge 412. According to certain embodiments, the anterior and posterior edges 410, 412 generally extend between the first and second edges 406, 408 along opposing sides of the outer edge 404 of the implant device 400. According to the illustrated embodiment, the anterior edge 410 and the posterior edge 412 can be separated from each other by an AP width in the AP direction (as indicated by the "AP" direction in FIG. 8A). The AP width can, according to certain embodiments, correspond to the maximum width of the implant device 400 in the AP direction. According to the embodiments shown in FIGS. 8A and 8B, the aspect ratio of the AP width to the ML width of the implant device 400, as indicated by "AP:MP" in FIG. 8A, can be about 1.1:1 to about 1.5:1, and more specifically, about 1.15:1 to 1.5:1, among other ratios. According to other embodiments, the aspect ratio of the AP width to the ML width of the implant device 400 can be from about 1.1:1 to about 1.4:1.

The lateral curve 402 of the implant can have a curvature radius of about 55 percent to about 70 percent of the ML width. Further, according to certain embodiments, the lateral curve 402 may extend along the anterior and posterior edges 410, 412 at a linear distance of about 0 percent to about 10 percent of the ML width from the first edge 406 and continue along the second edge 408. According to certain embodiments, one or both of the anterior and posterior edges 410, 412 can each include transition surfaces 414 that extend between the first edge 406 and the beginning of the curves 410, 412. Thus, according to certain embodiments, the transition surfaces 414, if any, can have a length greater than 0 percent to about 10 percent of the ML width. Further, the tangency of the lateral curve 402 to the first edge 406 can be within about 10 percent anterior-posterior of the midline of the second edge 408.

Figure 9A:
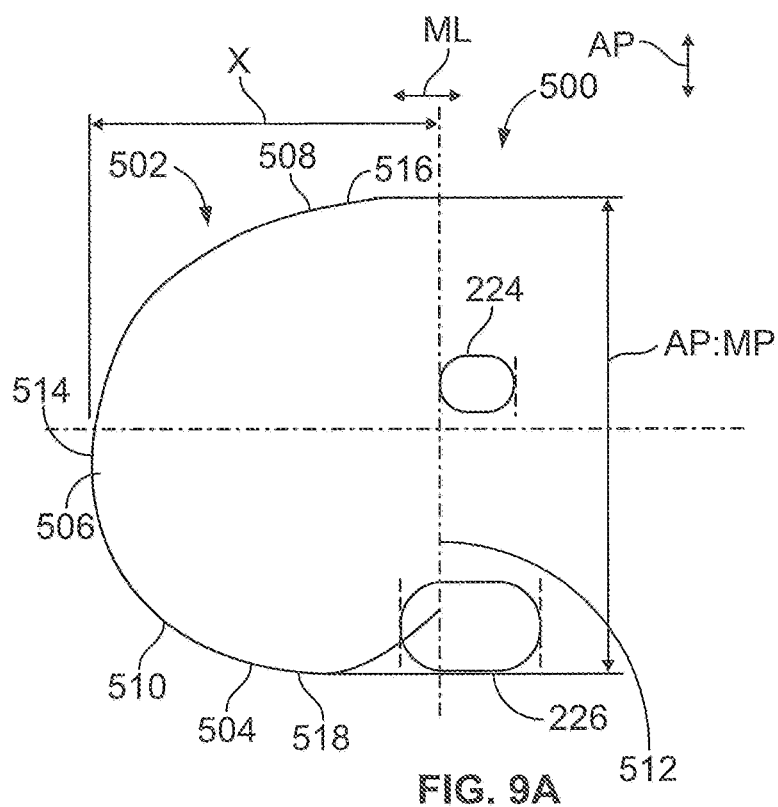
FIG. 9A illustrates a proximal side view of a lateral unicondylar tibia implant having at least three lateral curves according to certain embodiments of the present application.
Figure 9B:
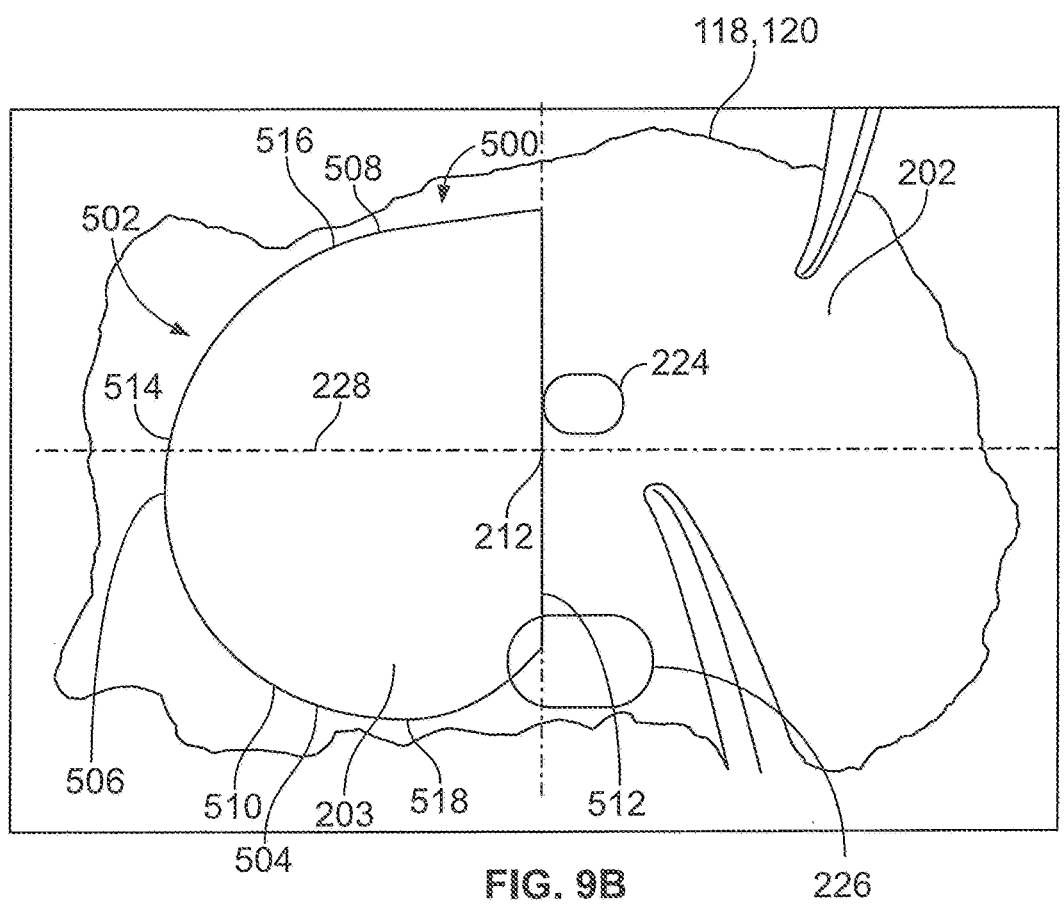
FIG. 9B illustrates the lateral unicondylar tibia implant(s) depicted in FIG. 9A and certain identified geometries of the implant(s) superimposed over an exemplary proximal tibia portion of a tibia.

FIG. 9A illustrates a proximal side view of an embodiment of a lateral unicondylar tibia implant device 500 having at least three lateral curves 502, which, in the illustrated embodiment, includes a posterior curve 504, a lateral curve 506, and an anterior curve 508. Further, FIG. 9B illustrates the lateral unicondylar tibia implant device 500 depicted in FIG. 9A superimposed over an exemplary proximal tibia portion of a tibia 118. While FIGS. 9A and 9B illustrate a lateral unicondylar tibia implant device 500 for a lateral compartment 203 of tibia 118 for the left knee, similar features also may be utilized for a lateral compartment of a tibia for the right knee, wherein the location or orientation of the depicted lateral unicondylar tibia implant device 500 can be adjusted to accommodate the change in hand from left to right.

The implant device 500 shown in FIGS. 9A and 9B includes an outer edge 510 having a first edge 512 and a second edge 514 at opposing sides of the implant device 500. While the first edge 512 is depicted in FIGS. 9A and 9B as being a relatively straight edge, the first edge 512 can have a variety of other configurations such as, for example, configurations that generally follow or otherwise provide clearance from the soft tissue boundaries of the tibial spine. For example, according to certain embodiments, the first edge 512 can be straight, curved, and/or scalloped, as well as various combinations thereof, among other shapes and configurations. Further, as shown in FIG. 9A, the first edge 512 is closer to the center of the tibia 118 than the second edge 514, and thus the first edge 512 can be considered bone facing. According to certain embodiments, the first edge 512 can be configured to be generally parallel to the tibia spine or AP tibia axis 212 of the tibia 118. However, alternatively, according to certain embodiments, the first edge 512 of the implant device 500 can be angled anterior to posterior relative to the AP tibia axis 212, in a manner that may facilitate the first edge 512 following a lateral edge of the ACL 224 and PCL 226. Further, as. with other portions of the outer edge 510 and other implants discussed herein, transition surfaces, including curves, edge blends, and/or straight lines, as well as a combination thereof, also can be present where otherwise non-tangent edges may occur.

Additionally, in the depicted embodiment, the first edge 512 and second edge 514 can be configured to provide the implant device 500 with a ML width in the ML direction (as indicated by the "ML" direction in FIG. 9A) that, for purposes of discussion, is identified in FIG. 9A as a length of "X". The ML width can, according to certain embodiments, represent the maximum ML width of the implant device 500 in the ML direction.

The outer edge 510 of the implant device 500 also can include an anterior edge 516 and a posterior edge 518. According to certain embodiments, the anterior and posterior edges 516, 518 generally extend between the first and second edges 512, 514 along opposing sides of the outer edge 510 of the implant device 500. According to the illustrated embodiment, the anterior edge 516 and the posterior edge 518 can be separated from each other by an AP width in the AP direction. (as indicated by the "AP" direction in FIG. 9A). The AP width can, according to certain embodiments, correspond to the maximum width of the implant device 500 in the AP direction. According to the embodiments shown in FIGS. 9A and 9B, the aspect ratio of the AP width to the ML width (as indicated by "AP:MP" in FIG. 9A) of the implant device 500 can be about 1.1:1 to about 1.5:1, and more specifically, about 1.1:1 to about 1.4:1, among other ratios.

The posterior curve 504 may extend along at least a portion of the posterior edge 518. For example, according to certain embodiments, the posterior curve 504 can begin at the first edge 512, or may begin within a linear distance of about 20 percent of the ML width from the first edge 512. Additionally, according to certain embodiments, the posterior curve 504 can continue from the posterior edge 518 and extend along at least a portion of the second edge 514. Further, according to certain embodiments, the posterior curve 504 can have a radius of curvature that is smaller than the radii of curvature of each of the outer and anterior curves 506, 508. For example, according to certain embodiments, the posterior curve 504 can have a radius of curvature that is about 75 percent to 100 percent the ML width.

The lateral curve 506 of the implant device 500 can generally be positioned between the anterior curve 508 and the posterior curve 504 and have a radius of curvature of about 55 percent to about 70 percent of the ML width. Thus, the radius of curvature of the lateral curve 506 can be greater than that of the posterior curve 504, as discussed above, but less than that of the anterior curve 508, as discussed below. Additionally, transition surfaces, if any, can be included to provide a transition between the lateral curve 506 and the posterior curve 504 and/or the lateral curve 506 and the anterior curve 508. According to certain embodiments, the lateral curve 506 can extend from a junction with the posterior curve 504 and extend along the second edge and through a tangency with the second edge 514. Further, the tangency of the lateral curve 506 with the midline of the second edge 514 can be within 0 percent to about 20 percent of the ML width posterior of the midline. Additionally, the lateral curve 506 can continue extending along at least the second edge 514 of the implant device 500 and end at a junction with the anterior curve 508, which can occur along the second edge 514 and/or the anterior edge 516. According to the illustrated embodiment, the junction of the outer and anterior curves 506, 508 is at a location that is, in a linear direction, about 30 percent to about 75 percent of the ML width away from the first edge 512.

The anterior curve 508 may extend along at least a portion of the anterior edge 516. For example, according to certain embodiments, the anterior curve 508 can begin at the first edge 512, or may begin within a linear distance of about 20 percent of the ML width from the first edge 512. Additionally, according to certain embodiments, the anterior curve 508 can continue from the anterior edge 516 and extend along at least a portion of the second edge 514. Further, according to certain embodiments, the anterior curve 508 can have a radius of curvature that is greater than the radii of curvature of each of the outer and posterior curves 506, 504. For example, according to certain embodiments, the anterior curve 508 can have an infinite radius of curvature such that, rather than being curved, the anterior curve 508 and/or the anterior edge 516 are generally straight. Further, according to certain embodiments, as shown in FIGS. 9A and 9B, the implant device 500 can generally have a "tear drop" shape.

Figure 10A:
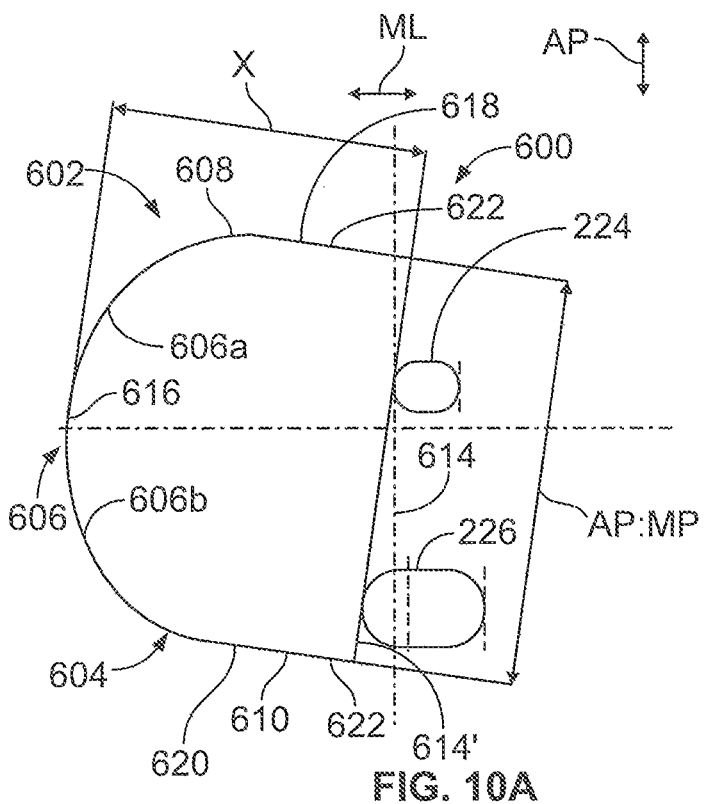
FIG. 10A illustrates a proximal side view of a lateral unicondylar tibia implant having up to four lateral curves according to certain embodiments of the present application.
Figure 10B:
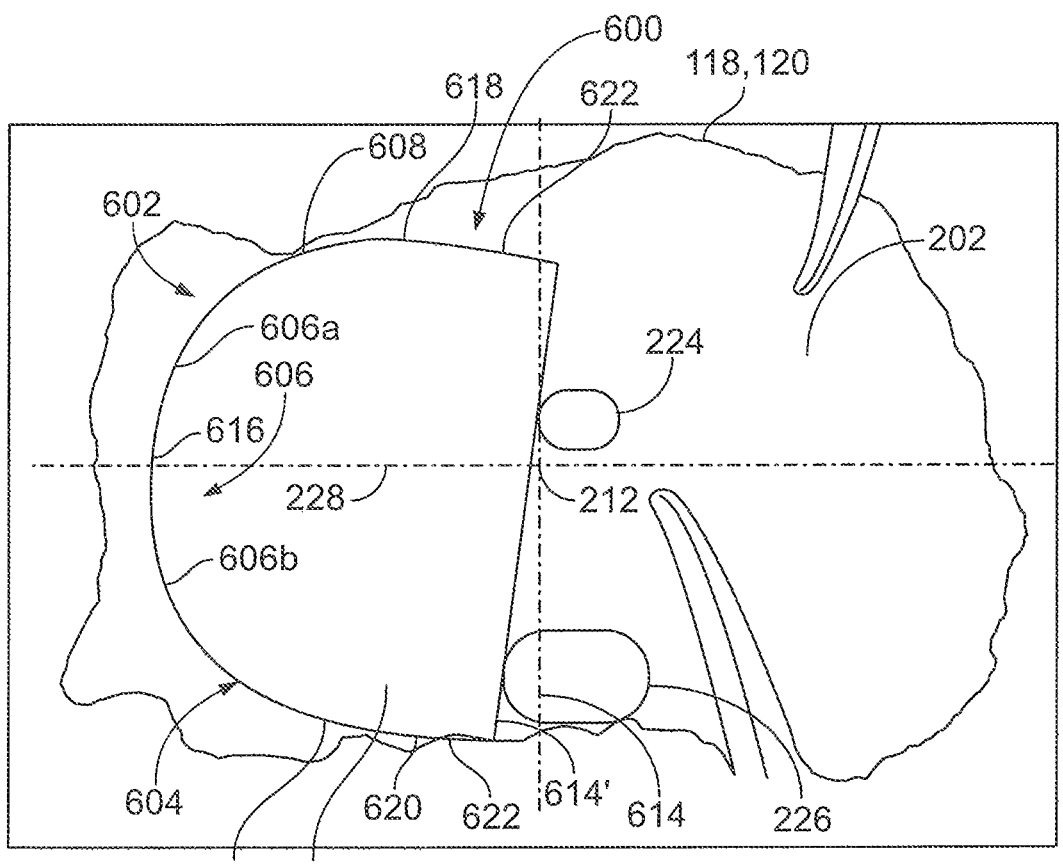
FIG. 10B illustrates the lateral unicondylar tibia implant(s) depicted in FIG. 10A and certain identified geometries of the implant(s) superimposed over an exemplary proximal tibia portion of a tibia.

FIG. 10A illustrates a proximal side view of an embodiment of a lateral unicondylar tibia implant device 600 having up to four lateral curves 602, which, in the illustrated embodiment, includes a posterior curve 604, one or more lateral curves 606, and an anterior curve 608. Further, FIG. 10B illustrates the lateral unicondylar tibia implant device 600 depicted in FIG. 10A superimposed over an exemplary proximal tibia portion of a tibia 118. While FIGS. 10A and 10B illustrate a lateral unicondylar tibia implant device 600 for a lateral compartment 203 of a tibia 118 for the left knee, similar features also may be utilized for a lateral compartment of a tibia for the right knee, wherein the location or orientation of the depicted lateral unicondylar tibia implant device 600 can be adjusted to accommodate the change in hand from left to right.

The implant device 600 shown in FIGS. 10A and 10B includes an outer edge 610 having a first edge 614, 614' and a second edge 616 at opposing sides of the implant device 600. While the first edge 614, 614' is depicted in FIGS. 10A and 10B as being a relatively straight edge, the first edge 614, 614' can have a variety of other configurations such as, for example, configurations that generally follow or otherwise provide clearance from the soft tissue boundaries of the tibial spine. For example, according to certain embodiments, the first edge 614, 614' can be straight, curved, and/or scalloped, as well as various combinations thereof, among other shapes and configurations. Further, as shown in FIG. 10A, the first edge 614, 614' is closer to the center of the tibia 118 than the second edge 616, and thus the first edge 614, 614' can be considered bone facing. According to certain embodiments, the first edge 614 can be configured to be generally parallel to the tibia spine or AP tibia axis 212 of the tibia 118. However, alternatively, according to certain embodiments, the first edge 614' of the implant device 600 can be angled anterior to posterior relative to the AP tibia axis 212, in a manner that may facilitate the first edge 614' following a lateral edge of the ACL 224 and PCL 226. Further, as with other portions of the outer edge 610 and other implants discussed herein, transition surfaces, including curves, edge blends, and/or straight lines, as well as combinations thereof, also can be present where otherwise non-tangent edges may occur.

In the depicted embodiment, the first edge 614, 614' and the second edge 616 can be configured to provide the implant device 600 with a ML width in the ML direction (as indicated by the "ML" direction in FIG. 10A) that, for purposes of discussion, is identified in FIG. 10A as "X". The ML width can, according to certain embodiments, represent the maximum ML width of the implant device 600 generally in the ML direction. For example, according to the embodiment depicted in FIG. 10A, the ML width may be the maximum width between the first and second edges 614, 614', 616 along a line that, in the illustrated embodiment, is generally perpendicular to the first edge 614, 614'.

The outer edge 610 of the implant device 600 also can include an anterior edge 618 and a posterior edge 620. According to certain embodiments, the anterior and posterior edges 618, 620 generally extend between the first and second edges 614, 614', 616 along opposing sides of the outer edge 610 of the implant device 600. According to the illustrated embodiment, the anterior edge 618 and the posterior edge 620 can be separated from each other by an AP width in the AP direction (as indicated by the "AP" direction in FIG. 10A). The AP width can, according to certain embodiments, correspond to the maximum width of the implant device 600 in the AP direction. For example, according to the embodiment depicted in FIG. 10A, the AP width may be the width between the anterior and posterior edges 618, 620 along a line that is generally perpendicular to the measurement used for the ML width and/or may be generally parallel to the illustrated first edge 614, 614'. According to the embodiments shown in FIGS. 10A and 10B, the aspect ratio of the AP width to the ML width (as indicated by "AP:MP" in FIG. 10A) of the implant device 600 can be about 1.1:1 to about 1.5:1, and more specifically, about 1.1:1 to about 1.4:1, among other ranges.

The posterior curve 604 may begin, or stop, along at least a portion of the posterior edge 620. For example, according to certain embodiments, the posterior curve 604 can begin at a linear distance of about 10 percent to about 60 percent of the ML width from the first edge 614, 614'. As shown in FIG. 10A, according to certain embodiments, the posterior curve 604 can be coupled to the first edge 614, 614' by a transition surface 622 such as, for example, a straight or curved line. Further, the posterior curve 604 can, at generally the most posterior portion of the second edge 616, be joined to one of the one or more lateral curves 606. According to certain embodiments, such a junction of the posterior curve to a lateral curve 606 can include a transition surface that joins the posterior and the lateral curves 604, 606. Such a transitional surface can have a variety of different shapes and configurations such as, for example, being a relatively straight surface or have a radius of curvature that is greater than or less than the radius of curvature of the lateral curve 606 to which the transition surface is joined.

The one or more lateral curves 606 can begin at the junction with the posterior curve 604, extend through the tangency with the second edge 616 of the implant device 600, and end at a junction with the anterior curve 608. The tangency of the one or more lateral curves 606 with the midline of the second edge 616 is within 0 percent to about 20 percent of the ML width posterior of the midline. Further, similar to the junction between the posterior curve 604, the junction between the one or more lateral curves 606 and the anterior curve 608 can include a transition surface that joins the anterior and lateral curves 608, 606. Such a transitional surface can have a variety of different shapes and configurations such as, for example, being a relatively straight surface or have a radius of curvature that is greater than or less than the radius of curvature of the lateral curve 606 to which the transition surface is joined.

According to certain embodiments, the lateral curve 606 can comprise a single curve having a radius of curvature that is greater than the radii of curvature of the anterior and posterior curves 608, 604. Alternatively, according to other embodiments, the lateral curve 606 can comprise a first lateral curve 606 and a second lateral curve 606, the first lateral curve 606 generally extending between the posterior curve 604 and the second lateral curve 606, including any associated transition surfaces. Similarly, the second lateral curve 606 can extend between the first lateral curve 606 and the anterior curve 608, including any associated transition surfaces. Further, according to certain embodiments, the first and second lateral curves 606a, 606b can each have radii of curvature that are greater than the radii of curvature of the anterior and posterior curves 608, 604. Additionally, the radii of curvature for the first and second lateral curves 606a, 606b can be different such as, for example, the first lateral curve 606 having a radius of curvature that is greater than the radius of curvature of the second lateral curve 606.

The anterior curve 608 can begin, or stop, at or about the anterior edge 618 at a linear distance of about 10 percent to about 60 percent of the ML width from the first edge 614, 614'. As shown in FIG. 10A, according to certain embodiments, the anterior curve 608 can be coupled to the first edge 614, 614' by a transition surface 622 such as, for example, a straight or curved line.

Figure 11A:
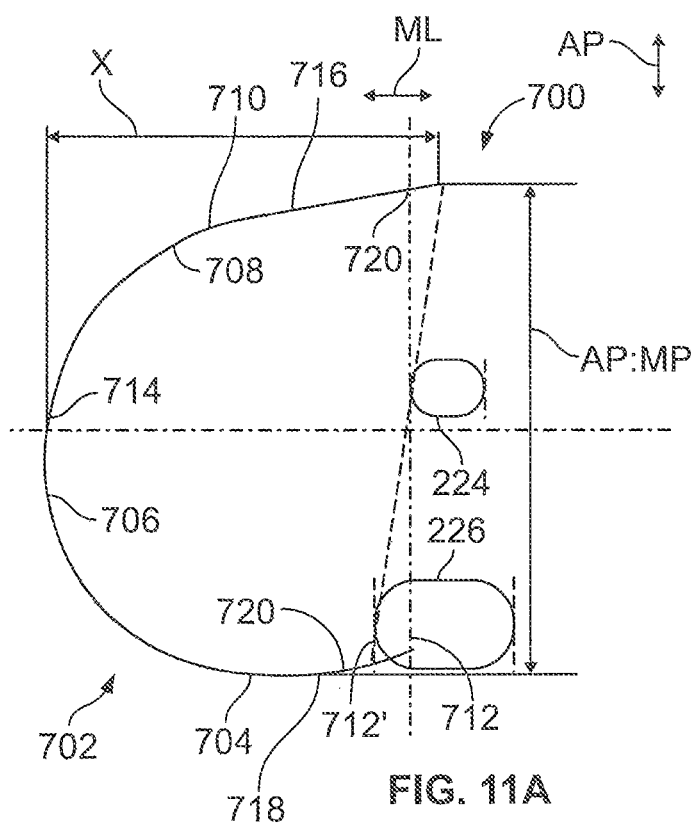
FIG. 11A illustrates a proximal side view of a lateral unicondylar tibia implant having at least three lateral curves and an angled posterior offset according to certain embodiments of the present application.
Figure 11B:
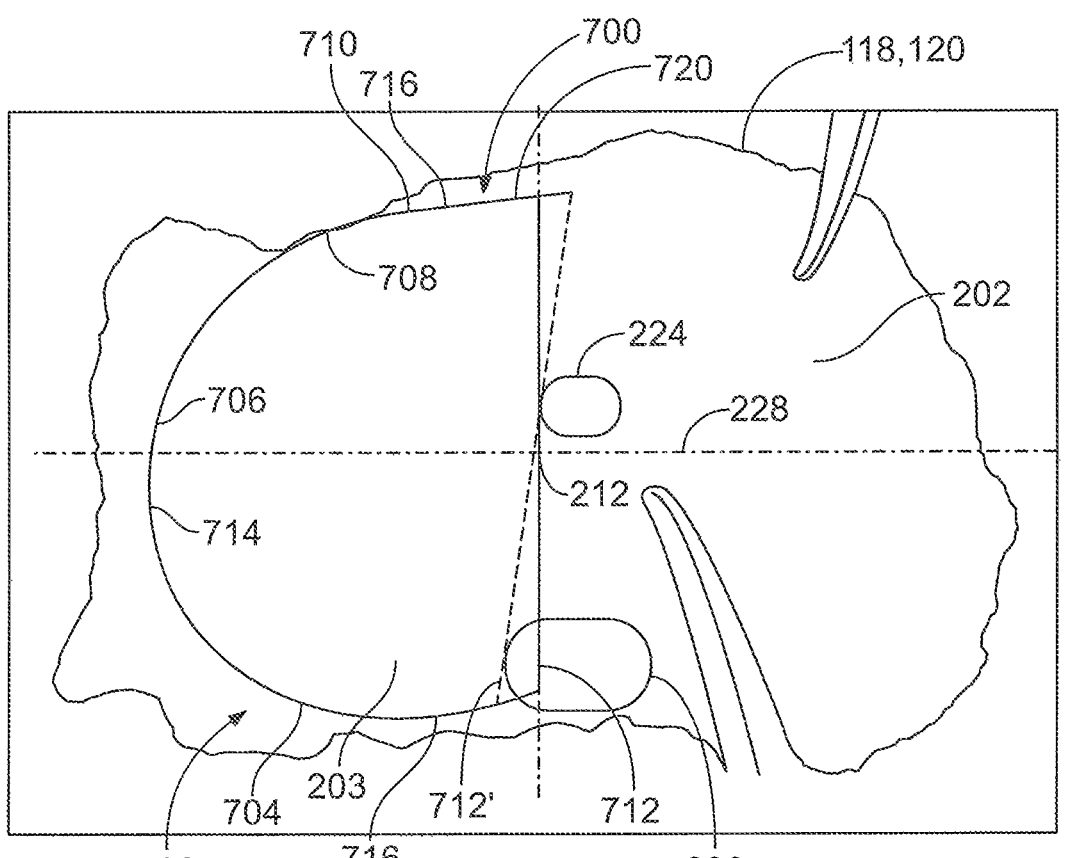
FIG. 11B illustrates the lateral unicondylar tibia implant(s) depicted in FIG. 11A and certain identified geometries of the implant(s) superimposed over an exemplary proximal tibia portion of a tibia.

FIG. 11A illustrates a proximal side view of an embodiment of a lateral unicondylar tibia implant device 700 having at least three lateral curves 702 and an angled posterior offset. The three lateral curves 702 can include a posterior curve 704, a lateral curve 706, and an anterior curve 708. Further, FIG. 11B illustrates the lateral unicondylar tibia implant device 700 depicted in FIG. 11A superimposed over an exemplary proximal tibia portion of a tibia 118. While FIGS. 11A and 11B illustrate a lateral unicondylar tibia implant device 700 for a lateral compartment 203 of a tibia 118 for the left knee, similar features also may be utilized for a lateral compartment of a tibia for the right knee, wherein the location or orientation of the depicted lateral unicondylar tibia implant device 700 can be adjusted to accommodate the change in hand from left to right.

The implant device 700 shown in FIGS. 11A and 11B includes an outer edge 710 having a first edge 712, 712' and a second edge 714 at opposing sides of the implant device 700. While the first edge 712, 712' is depicted in FIGS. 11A and 11B as being a relatively straight edge, the first edge 712, 712' can have a variety of other configurations such as, for example, configurations that generally follow or otherwise provide clearance from the soft tissue boundaries of the tibial spine. For example, according to certain embodiments, the first edge 712, 712' can be straight, curved, and/or scalloped, as well as various combinations thereof, among other shapes and configurations. Further, as shown in FIG. 11A, the first edge 712, 712' is closer to the center of the tibia 118 than the second edge 714, and thus the first edge 712, 712' can be considered bone facing. According to certain embodiments, the first edge 712 can be configured to be generally parallel to the tibia spine or AP tibia axis 212 of the tibia 118. However, alternatively, according to certain embodiments, the first edge 712' of the implant device 700 can be angled anterior to posterior relative to the AP tibia axis 212, in a manner that may facilitate the first edge 712 following a lateral edge of the ACL 224 and PCL 226. Further, as with other portions of the outer edge 710 and other implants discussed herein, transition surfaces, including curves, edge blends, and/or straight lines, as well as a combination thereof, also can be present where otherwise non-tangent edges may occur.

Additionally, in the depicted embodiment, the first edge 712, 712' and second edge 714 can be configured to provide the implant device 700 with a ML width in the ML direction (as indicated by the "ML" direction in FIG. 11A) that, for purposes of discussion, is identified in FIG. 11A as "X". The ML width can, according to certain embodiments, represent the maximum ML width of the implant device 700 generally in the ML direction. For example, according to the embodiment depicted in FIG. 11A, the ML width may be the maximum width between the first and second edges 712, 712', 714 along a line that is generally perpendicular to the first edge 712, 712'.

The outer edge 710 of the implant device 700 also can include an anterior edge 716 and a posterior edge 718. According to certain embodiments, the anterior and posterior edges 716, 718 generally extend between the first and second edges 712, 712', 714 along opposing sides of the outer edge 710 of the implant device 700. According to the illustrated embodiment, the anterior edge 716 and the posterior edge 718 can be separated from each other by an AP width in the AP direction (as indicated by the "AP" direction in FIG. 11A). The AP width can, according to certain embodiments, correspond to the maximum width of the implant device 700 in the AP direction. For example, according to the embodiment depicted in FIG. 11A, the AP width may be the width between the anterior and posterior edges 716, 718 along a line that is generally perpendicular to the measurement used for the ML width and/or may be generally parallel to the first edge 712, 712'. According to the embodiments shown in FIGS. 11A and 11B, the aspect ratio of the AP width to the ML width (as indicated by "AP:MP" in FIG. 11A) of the implant device 700 can be about 1.1:1 to about 1.5:1, and more specifically, about 1.1:1 to about 1.4:1, among other ratios. Further, transition surfaces, including straight and curved surfaces and edge blends can be present along the outer edge 710 at least at locations where otherwise non-tangent edges may occur.

The posterior curve 704 may begin, or stop, along at least a portion of the posterior edge 718. For example, according to certain embodiments, the posterior curve 704 can begin at a linear distance of about 20 percent of the ML width from the first edge 712, 712'. Further, as shown in FIG. 11A, according to certain embodiments, the posterior curve 704 can be coupled to the first edge 712, 712' by a transition surface 720 such as, for example, a straight or curved line. According to the illustrated embodiment, the transition surface between the posterior curve 704 and the first edge 712, 712' can be angled from the first edge 712, 712' to the posterior curve 704 in a manner in which the transition surface 720 is joined to the posterior curve 704 at a posterior position than is offset from, or otherwise further in the posterior direction than, the junction between the transition surface 720 and the most posterior portion of the first edge 712, 712'.

The posterior curve 704 can extend along the second edge 714 to a location that is a linear distance away from the first edge 712, 712' that is about 70 percent to about 100 percent the ML width. Further, the posterior curve can have a radius of curvature that is greater than the radius of curvature of the lateral curve 706 but smaller than the radius of curvature of the anterior curve 708. Further, the posterior curve 704 can be joined to the lateral curve 706 by one or more transition surfaces 720 including, for example, smaller radius blend between the posterior and lateral curves 704, 706. The tangency of the outer and posterior curves 706, 704, or lateral edge with the midline of the second edge 714, can be at a linear distance that is within 0 percent to about 20 percent of the ML width posterior of the midline.

The lateral curve 606 can have a radius of curvature that is smaller than the radii of curvature of the posterior and anterior curves 708, 704, and can begin at the junction with the posterior curve 704, as previously discussed. Further, the lateral curve 706 can extend through the tangency with the second edge of the implant device 700 and extend to a junction of the anterior curve 708, which can be generally located at a linear distance of about 40 percent to about 100 percent the ML width from the first edge 712, 712'. The lateral curve 606 also can be joined to the anterior curve 708 by one or more transition surfaces 720 including, for example, a smaller radius blend between the anterior and lateral curves, 708, 706. The anterior curve 708 can begin at a linear distance of about 20 percent of the ML width from the first edge 712, 712' and extend to the lateral curve 706. Further, the anterior curve 708 can have a radius of curvature that is larger than the lateral curve 706 including, for example, a radius of curvature up to, and including, an infinite radius (e.g., a straight edge). Additionally, according to certain embodiments, a transition surface 720 can extend between the first edge 712, 712' and the anterior curve 708.

Figure 12A:
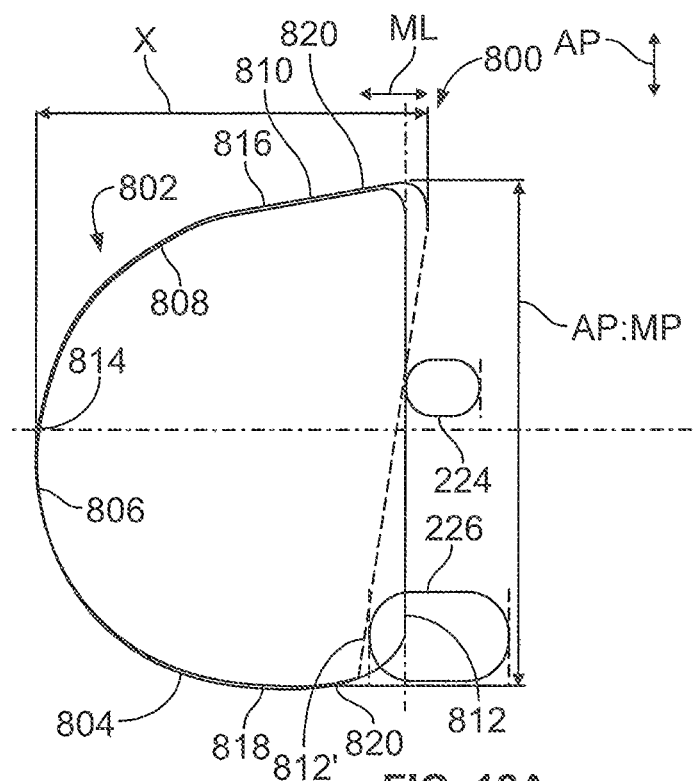
FIG. 12A illustrates a proximal side view of a lateral unicondylar tibia implant having at least three lateral curves and an angled posterior offset according to certain embodiments of the present application.
Figure 12B:
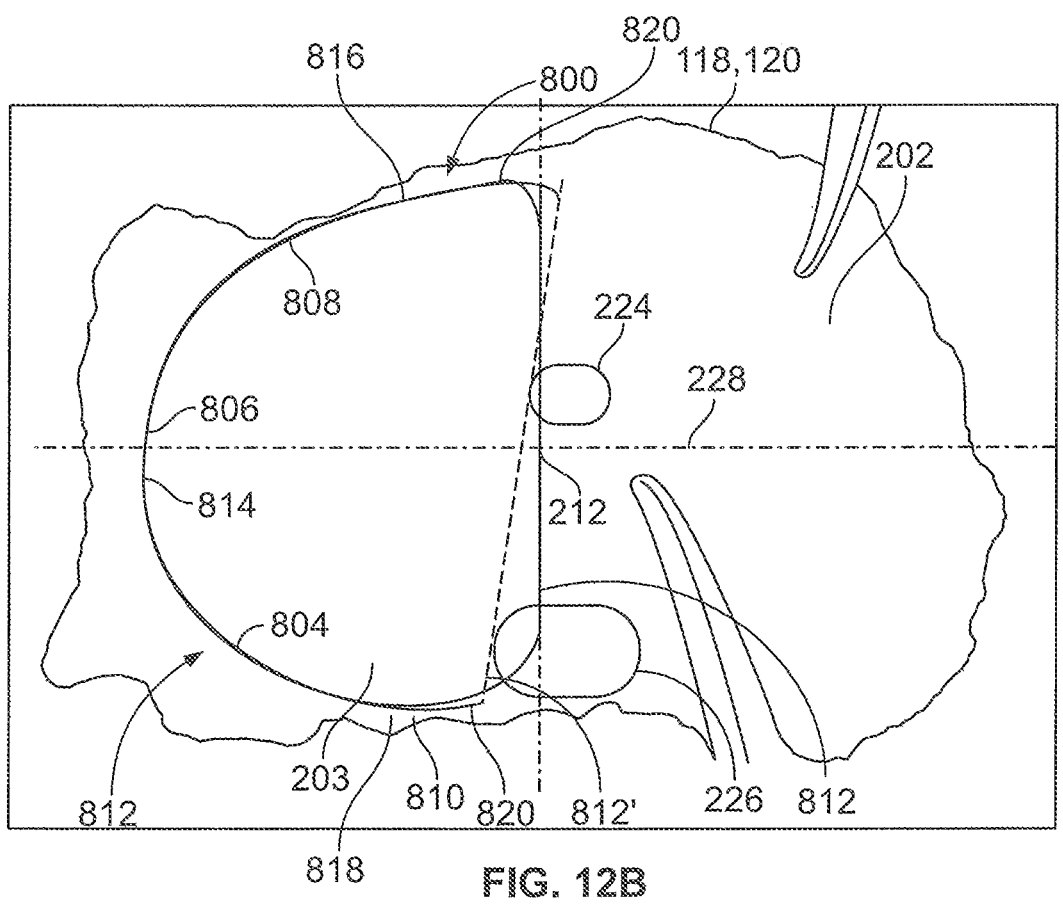
FIG. 12B illustrates the lateral unicondylar tibia implant(s) depicted in FIG. 12A and certain identified geometries of the implant(s) superimposed over an exemplary proximal tibia portion of a tibia.

FIG. 12A illustrates a proximal side view of an embodiment of a lateral unicondylar tibia implant device 800 having at least three lateral curves 802 and an angled posterior offset. The three lateral curves 802 can include a posterior curve 804, a medial lateral 806, and an anterior curve 808. Further, FIG. 12B illustrates the lateral unicondylar tibia implant device 800 depicted in FIG. 12A superimposed over an exemplary proximal tibia portion of a tibia 118. While FIGS. 12A and 12B illustrate a lateral unicondylar tibia implant device 800 for a lateral compartment 203 of a tibia 118 for the left knee, similar features also may be utilized for a lateral compartment of a tibia for the right knee, wherein the location or orientation of the depicted lateral unicondylar tibia implant device 800 can be adjusted to accommodate the change in hand from left to right.

The implant device 800 shown in FIGS. 12A and 12B includes an outer edge 810 having a first edge 812, 812' and a second edge 814 at opposing sides of the implant device 800. While the first edge 812, 812' is depicted in FIGS. 12A and 12B as being a relatively straight edge, the first edge 812, 812' can have a variety of other configurations such as, for example, configurations that generally follow or otherwise provide clearance from the soft tissue boundaries of the tibial spine. For example, according to certain embodiments, the first edge 812, 812' can be straight, curved, and/or scalloped, as well as various combinations thereof, among other shapes and configurations. Further, as shown in FIG. 12A, the first edge 812 is closer to the center of the tibia 118 than the second edge 814, and thus the first edge 812 can be considered bone facing. According to certain embodiments, the first edge 812 can be configured to be generally parallel to the tibia spine or AP tibia axis 212 of the tibia 118. However, alternatively, according to certain embodiments, the first edge 812' of the implant device 800 can be angled anterior to posterior relative to the AP tibia axis 212 in a manner that may facilitate the first edge 812' following a lateral edge of the ACL 224 and PCL 226.

Additionally, in the depicted embodiment, the first edge 812, 812' and second edge 814 may be configured to provide the implant device 800 with a ML width in the ML direction (as indicated by the "ML" direction in FIG. 12A) that, for purposes of discussion, is identified in FIG. 12A as "X". The ML width can, according to certain embodiments, represent the maximum ML width of the implant device 800 generally in the ML direction. For example, according to the embodiment depicted in FIG. 12A, the ML width can be the maximum width between the first and second edges 812, 812', 814 along a line that is generally perpendicular to the first edge 812.

The outer edge 810 of the implant device 800 also can include an anterior edge 816 and a posterior edge 818. According to certain embodiments, the anterior and posterior edges 816, 818 generally extend between the first and second edges 812, 812', 814 along opposing sides of the outer edge 810 of the implant device 800. According to the illustrated embodiment, the anterior edge 816 and the posterior edge 818 can be separated from each other by an AP width in the AP direction (as indicated by the "AP" direction in FIG. 12A). The AP width can, according to certain embodiments, correspond to the maximum width of the implant device 800 in the AP direction. For example, according to the embodiment depicted in FIG. 12A, the AP width can be the width between the anterior and posterior edges 816, 818 along a line that is generally perpendicular to the measurement used for the ML width and/or may be generally parallel to the first edge 812, 812'. According to the embodiments shown in FIGS. 12A and 12B, the aspect ratio of the AP width to the ML width (as indicated by "AP:MP" in FIG. 12A) of the implant device 800 can be about 1.1:1 to about 1.5:1, and more specifically, about 1.1:1 to about 1.4:1, among other ranges. Further, transition surfaces, including straight and curved surfaces and edge blends can be present along the outer edge 810 at least at locations where non-tangent edges may otherwise occur.

The posterior curve 804 may begin, or stop, along at least a portion of the posterior edge 818. For example, according to certain embodiments, the posterior curve 804 can begin at a linear distance of about 20 percent of the ML width from the first edge 812, 812'. Further, as shown in FIG. 12A, according to certain embodiments, the posterior curve 804 can be coupled to the first edge 812, 812' by a transition surface 820 such as, for example, a straight or curved line. According to the illustrated embodiment, the transition surface between the posterior curve 804 and the first edge 812, 812' can be angled from the first edge 812, 812' to the posterior curve 804 in a manner in which the transition surface 820 is joined to the posterior curve 804 at a posterior position than is offset from, or otherwise further in the posterior direction than, the junction between the transition surface 820 and the most posterior portion of the first edge 812, 812'.

The posterior curve 804 can extend along the second edge 814 to a location that is a linear distance away from the first edge 812, 812' that is about 40 percent to about 60 percent the ML width. Further, the posterior curve 804 can have a radius of curvature that is smaller than the radii of curvature of the outer and anterior curves 806, 808. Further, the posterior curve 804 can be joined to the lateral curve 806 by one or more transition surfaces 820 including, for example, smaller radius blend between the posterior and lateral curves 804, 806.

The lateral curve 806 can have a radius of curvature that is smaller than the radius of curvature of the anterior curve 808, can begin at the junction with the posterior curve 804, as previously discussed, and can extend through the tangency with the second edge 814 of the implant device 800. Further, the lateral curve 806 can extend to a junction of the anterior curve 808, which can be generally located at a linear distance of about 40 percent to about 60 percent the ML width from the first edge 812, 812'. The lateral curve 806 also can be joined to the anterior curve 808 by one or more transition surfaces 820 including, for example, a smaller radius blend between the anterior and lateral curves 808, 806. The tangency of the lateral curve 806 with the midline of the first edge 812, 812' is within 0 percent to about 20 percent of the ML width posterior of the midline. The anterior curve 808 can begin at a linear distance of about 20 percent of the ML width from the first edge 812, 812' and extend to the lateral curve 806. Further, the anterior curve 808 can have a radius of curvature that is larger than the lateral curve 806 including, for example, a radius of curvature up to, and including, an infinite radius (e.g., a straight edge). Further, according to certain embodiments, a transition surface 820 can extend between the first edge 812, 812' and the anterior curve 808.

Figure 13A:
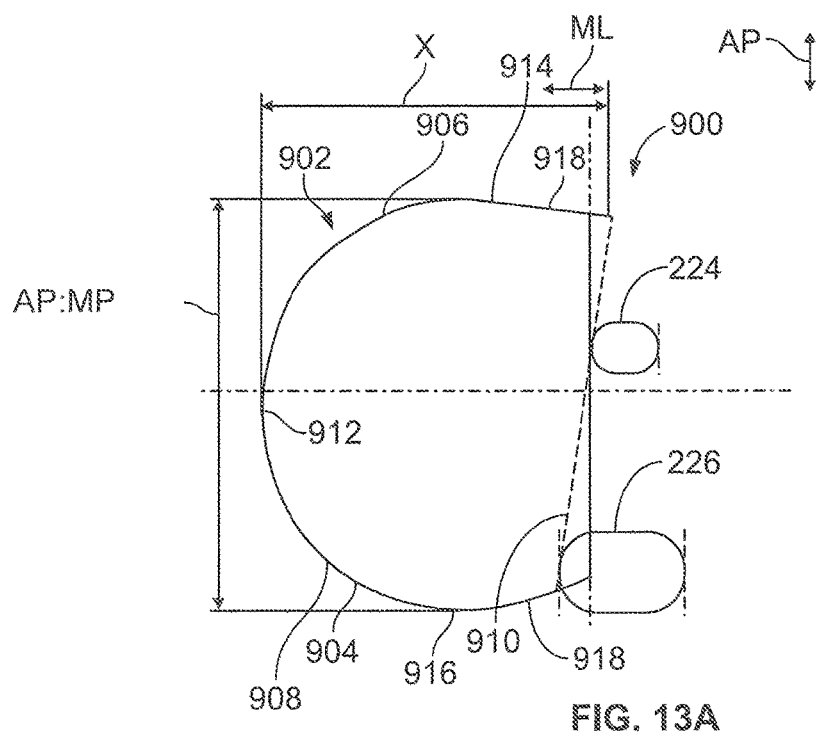
FIG. 13A illustrates a proximal side view of a lateral unicondylar tibia implant having at least two lateral curves according to certain embodiments of the present application.
Figure 13B:
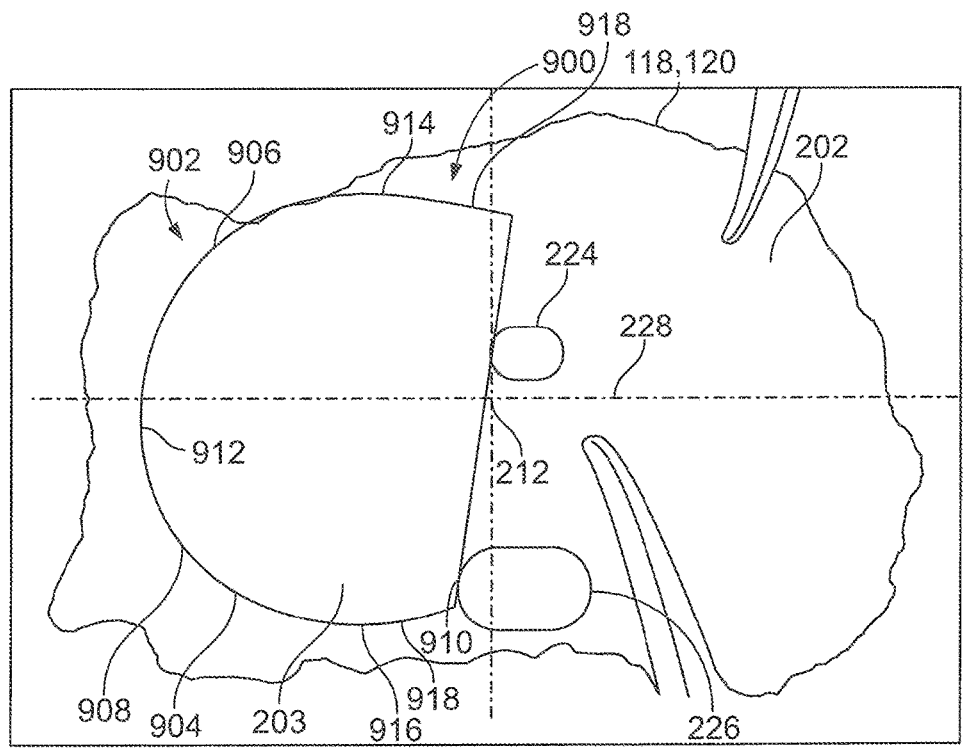
FIG. 13B illustrates the lateral unicondylar tibia implant(s) depicted in FIG. 13A and certain identified geometries of the implant(s) superimposed over an exemplary proximal tibia portion of a tibia.

FIG. 13A illustrates a proximal side view of an embodiment of a lateral unicondylar tibia implant device 900 having at least two lateral curves 902. The two lateral curves 902 can include a posterior curve 904 and an anterior curve 906. Further, FIG. 13B illustrates the lateral unicondylar tibia implant device 900 depicted in FIG. 13A superimposed over an exemplary proximal tibia portion of a tibia 118. While FIGS. 13A and 13B illustrate a lateral unicondylar tibia implant device 900 for a lateral compartment 203 of a tibia 118 for the left knee, similar features also can be utilized for a lateral compartment of a tibia for the right knee, wherein the location or orientation of the depicted lateral unicondylar tibia implant device 900 can be adjusted to accommodate the change in hand from left to right.

The implant device 900 shown in FIGS. 13A and 13B includes an outer edge 908 having a first edge 910 and a second edge 912 at opposing sides of the implant device 900. Further, as shown in FIG. 13A, the first edge 910 is closer to the center of the tibia 118 than the second edge 912, and thus the first edge 910 can be considered bone facing. According to certain embodiments, the first edge 910 can be configured to be generally parallel to the tibia spine or AP tibia axis 212 of the tibia 118. However, alternatively, according to certain embodiments, the first edge 910 of the implant device 900 can be angled anterior to posterior relative to the AP tibia axis 212, in a manner that may facilitate the first edge 910 following a lateral edge of the ACL 224 and PCL 226. Further, as with other portions of the outer edge 908 and other implants discussed herein, transition surfaces, including curves, edge blends, and/or straight lines, as well as a combination thereof, also can be present where otherwise non-tangent edges may occur.

Additionally, in the depicted embodiment, the first edge 910 and the second edge 912 can be configured to provide the implant device 900 with a ML width in the ML direction (as indicated by the "ML" direction in FIG. 13A) that, for purposes of discussion, is identified in FIG. 13A as a length of "X". The ML width can, according to certain embodiments, represent the maximum ML width of the implant device 900 generally in the ML direction. For example, according to the embodiment depicted in FIG. 13A, the ML width may be the maximum width between the first and second edges 910, 912 along a line that is generally perpendicular to the first edge 910.

The outer edge 908 of the implant device 900 also can include an anterior edge 914 and a posterior edge 916. According to certain embodiments, the anterior and posterior edges 914, 916 generally extend between the first and second edges 910, 912 along opposing sides of the outer edge 908 of the implant device 900. According to the illustrated embodiment, the anterior edge 914 and the posterior edge 916 can be separated from each other by an AP width in the AP direction (as indicated by the "AP" direction in FIG. 13A). The AP width can, according to certain embodiments, correspond to the maximum width of the implant device 900 in the AP direction. For example, according to the embodiment depicted in FIG. 13A, the AP width may be the width between the anterior and posterior edges 914, 916 along a line that is generally perpendicular to the measurement used for the ML width and/or may be generally parallel to the illustrated first edge 910. According to the embodiments shown in FIGS. 13A and 13B, the aspect ratio of the AP width to the ML width (as indicated by "AP:MP" in FIG. 13A) of the implant device 900 can be about 1.1:1 to about 1.5:1, and more specifically, about 1.1:1 to about 1.4:1, among other ranges. Further, transition surfaces, including straight and curved surfaces and edge blends can be present along the outer edge 908 at least at locations where non-tangent edges may otherwise occur.

The posterior curve 904 may begin, or stop, along at least a portion of the posterior edge 916. For example, according to certain embodiments, the posterior curve 904 can begin at a linear distance of about 20 percent of the ML width from the first edge 910. Further, as shown in FIG. 13A, according to certain embodiments, the posterior curve 904 can be coupled to the first edge 910 by a transition surface 918 such as, for example, a straight or curved line. According to the illustrated embodiment, the transition surface between the posterior curve 904 and the first edge 910 can be angled from the first edge 910 to the posterior curve 904 in a manner in which the transition surface 918 is joined to the posterior curve 904 at a posterior position than is offset from, or otherwise further in the posterior direction than, the junction between the transition surface 918 and the most posterior portion of the first edge 910.

Additionally, although the first edge 910 is depicted in FIGS. 13A and 13B as being a relatively straight edge, the first edge 910 can have a variety of other configurations such as, for example, configurations that generally follow or otherwise provide clearance from the soft tissue boundaries of the tibial spine. For example, according to certain embodiments, the first edge 910 can be straight, curved, and/or scalloped, as well as various combinations thereof, among other shapes and configurations.

The posterior curve 904 can have a radius of curvature that is smaller than the radius of curvature of the anterior curve 906, and can extend along the second edge 912 through the tangency with the second edge 912 of the implant device 900 generally to a junction with the anterior curve 906. Moreover, the posterior curve 904 can extend along the second edge 912 until the posterior curve 904 reaches a linear distance of about 20 percent to about 50 percent of the ML width from the first edge 910. Further, the junction between the posterior and anterior curves 916, 914 can include a transition surface such as, for example, a curved transition surface. According to certain embodiments, the transition surface between the posterior and anterior curves 916, 914 can have a radius of curvature that is larger than the radius of curvature of the posterior curve 904 but smaller than the radius of curvature of the anterior curve 906. Further, the tangency of the lateral curve 901 with the midline of the lateral edge is within about 0 percent to about 20 percent of the ML width posterior of the midline.

The anterior curve 906 can begin at a linear distance of about 20 percent of the ML width from the first edge 910 and extend to the posterior curve 904. According to such embodiments, a transition surface 918 can extend between the first edge 910 and the anterior curve 906. Additionally, according to certain embodiments, the anterior curve 906 can begin at about 20 percent of the ML width from the first edge 910 and be acute or at a right angle to the first edge 910. Further, the anterior curve 906 can have a radius of curvature up to, and including, an infinite radius (e.g., a straight edge).

Figure 14A:
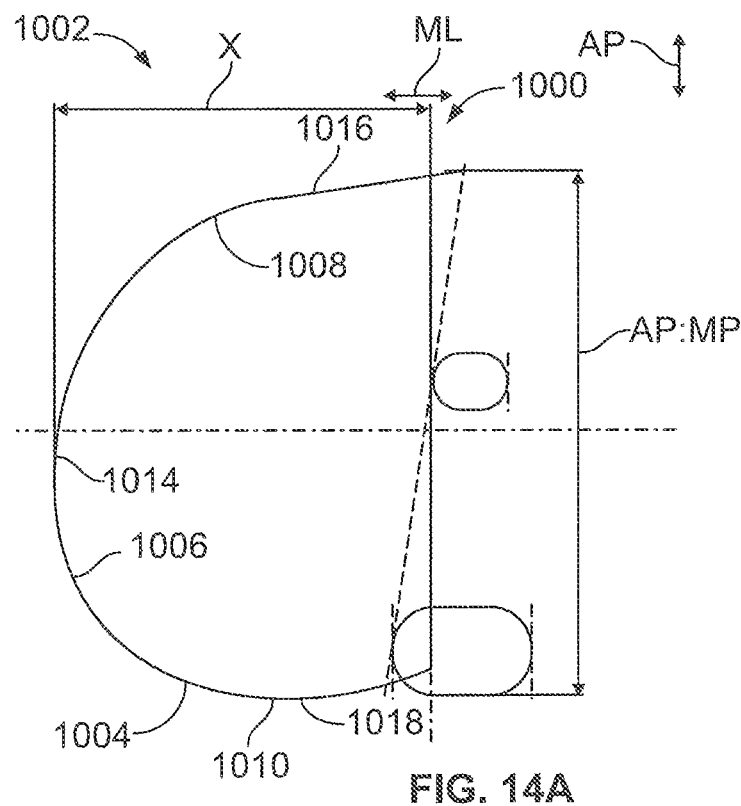
FIG. 14A illustrates a proximal side view of a lateral unicondylar tibia implant having at least three lateral curves according to certain embodiments of the present application.
Figure 14B:
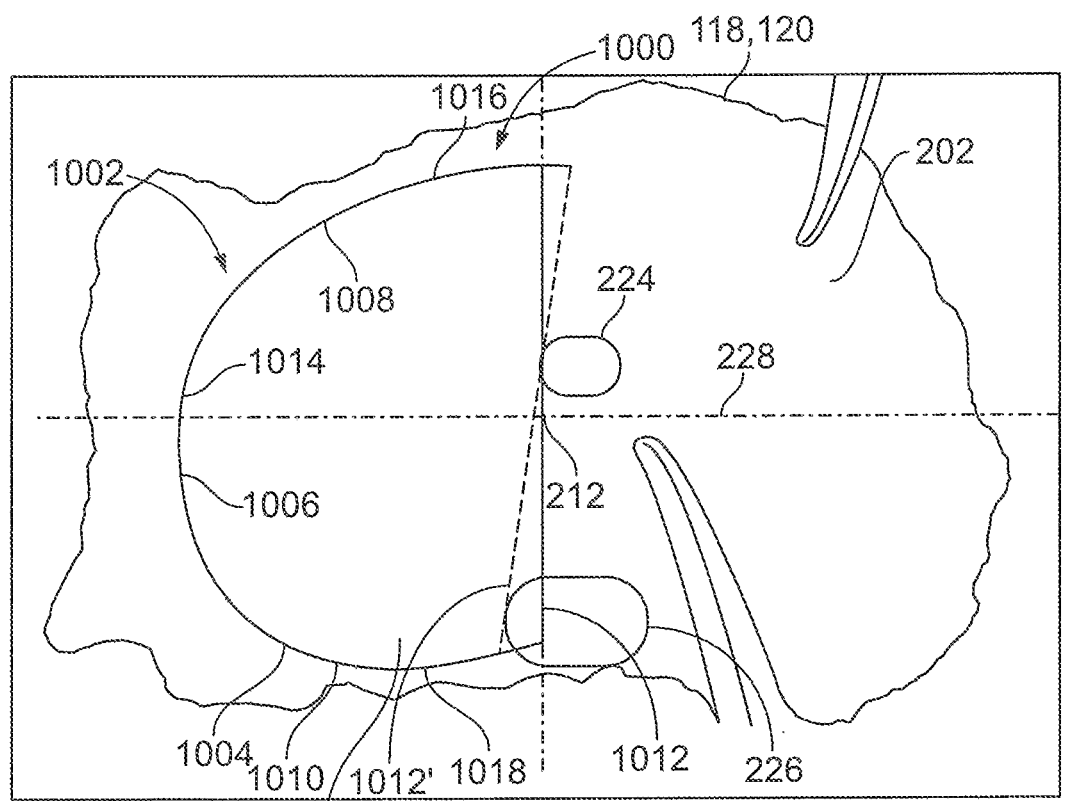
FIG. 14B illustrates the lateral unicondylar tibia implant(s) depicted in FIG. 14A and certain identified geometries of the implant(s) superimposed over an exemplary proximal tibia portion of a tibia.

FIG. 14A illustrates, a proximal side view of an embodiment of a lateral unicondylar tibia implant 1000 having at least three lateral curves 1002. The three lateral curves 1002 can include a posterior curve 1004, a lateral curve 1006, and an anterior curve 1008. Further, FIG. 14B illustrates the lateral unicondylar tibia implant 1000 depicted in FIG. 14A superimposed over an exemplary proximal tibia portion of a tibia 118. While FIGS. 14A and 14B illustrate a lateral unicondylar tibia implant 1000 for a lateral compartment 203 of a tibia 118 for the left knee, similar features also may be utilized for a lateral compartment of a tibia for the right knee, wherein the location or orientation of the depicted lateral unicondylar tibia implant 1000 can be adjusted to accommodate the change in hand from left to right.

The implant 1000 shown in FIGS. 14A and 14B includes an outer edge 1010 having a first edge 1012, 1012' and a second edge 1014 at opposing sides of the implant 1000. While the first edge 1012, 1012' is depicted in FIGS. 14A and 14B as being a relatively straight edge, the first edge 1012, 1012' can have a variety of other configurations such as, for example, configurations that generally follow or otherwise provide clearance from the soft tissue boundaries of the tibial spine. For example, according to certain embodiments, the first edge 1012, 1012' can be straight, curved, and/or scalloped, as well as various combinations thereof, among other shapes and configurations. Further, as shown in FIG. 14A, the first edge 1012, 1012' is closer to the center of the tibia 118 than the second edge 1014, and thus the first edge 1012 can be considered bone facing. According to certain embodiments, the first edge 1012 can be configured to be generally parallel to the tibia spine or AP tibia axis 212 of the tibia 118. However, alternatively, according to certain embodiments, the first edge 1012' of the implant 1000 can be angled anterior to posterior relative to the AP tibia axis 212, in a manner that may facilitate the first edge 1012' following a lateral edge of the ACL 224 and PCL 226. Further, as with other portions of the outer edge 1010 and other implants discussed herein, transition surfaces, including curves, edge blends, and/or straight lines, as well as a combination thereof, also can be present where otherwise non-tangent edges may occur.

Additionally, in the depicted embodiment, the first edge 1012, 1012' and second edge 1014 can be configured to provide the implant 1000 with a ML width in the ML direction (as indicated by the "ML" direction in FIG. 14A) that, for purposes of discussion, is identified in FIG. 14A as "X". The ML width can, according to certain embodiments, represent the maximum ML width of the implant 1000 generally in the ML direction. For example, according to the embodiment depicted in FIG. 14A, the ML width can be the maximum width between the first and second edges 1012, 1012', 1014 along a line that is generally perpendicular to the first edge 1012, 1012'.

The outer edge 1010 of the implant 1000 also can include an anterior edge 1016 and a posterior edge 1018. According to certain embodiments, the anterior and posterior edges 1016, 1018 generally extend between the first and second edges 1012, 1012', 1014 along opposing sides of the outer edge 1010 of the implant 1000. According to the illustrated embodiment, the anterior edge 1016 and the posterior edge 1018 can be separated from each other by an AP width in the AP direction (as indicated by the "AP" direction in FIG. 14A). The AP width can, according to certain embodiments, correspond to the maximum width of the implant 1000 in the AP direction. For example, according to the embodiment depicted in FIG. 14A, the AP width may be the width between the anterior and posterior edges 1016, 1018 along a line that is generally perpendicular to the measurement used for the ML width and/or may be generally parallel to the illustrated first edge 1012. According to the embodiments shown in FIGS. 14A and 14B, the aspect ratio of the AP width to the ML width (as indicated by "AP:MP" in FIG. 14A) of the implant 1000. can be about 1.1:1 to about 1.5:1, and more specifically, about 1.1:1 to about 1.4:1, among other ranges. Further, transition surfaces, including straight and curved surfaces and edge blends, can be present along the outer edge 1010 at least at locations where non-tangent edges may otherwise occur.

The posterior curve 1004 may begin, or stop, along at least a portion of the posterior edge 1018. For example, according to certain embodiments, the posterior curve 1004 can begin at a linear distance of about 25 percent to about 35 percent of the ML width from the first edge 1012, 1012'.

Further, as shown in FIG. 14A, according to certain embodiments, the posterior curve 1004 can be coupled to the first edge 1012, 1012' by a transition surface 1020 such as, for example, a straight or curved line. According to the illustrated embodiment, the transition surface between the posterior curve 1004 and the first edge 1012, 1012' can be angled from the first edge 1012, 1012' to the posterior curve 1004 in a manner in which the transition surface 1020. is joined to the posterior curve 1004 at a posterior position than is offset from, or otherwise further in the posterior direction, than the junction between the transition surface 1020 and the most posterior portion of the first edge 1012, 1012'. Further, the posterior curve 1004, which can have a radius of curvature that is smaller than the radii of curvature of the outer and anterior curves 1006, 1008, can extend along the second edge 1014 and end either tangent of the AP axis of the tibia 118 at the most lateral portion of the, second edge 1014 or at a section defining the second edge 1014, and more specifically, end at a straight edge or relatively large transition radius that passes through the lateral most point between the posterior and lateral curves.

The lateral curve 1006 can have a radius of curvature that is smaller than the radii of curvature of the anterior curve 1008, can begin either at the junction with the posterior curve 1004 or at a section defining the second edge 1014 such as, for example, begin at a straight edge or relatively large transition radius that passes through the lateral most point between the posterior and lateral curves. Further, the lateral curve 1006 can extend to a junction with the anterior curve 1008, which can be generally located at a linear distance of about 40 percent to about 60 percent the ML width from the first edge 1012, 1012'. The lateral curve 1006 also can be joined to the anterior curve 1008 by one or more transition surfaces 1020 including, for example, a smaller radius blend between the anterior and lateral curves 1008, 1010. The tangency of the outer and posterior curves 1006, 1004 or second edge 1014 with the midline of the first edge 1012, 1012' can be within about 0 percent to about 20 percent of the ML width posterior of the midline. The anterior curve 1008 can begin at a linear distance of about 20 percent of the ML width from the first edge 1012, 1012' and extend to the lateral curve 1006. Further, according to certain embodiments, a transition surface 1020 can extend between the first edge 1012, 1012' and the anterior curve 1008.

An aspect of an embodiment of the present application is an implant device for implantation on a tibia that can include an outer edge including a first edge, a second edge, an anterior edge, and a posterior edge. At least a portion of the first and second edges can be separated by an ML width, and at least a portion of the anterior and posterior edges being separated by an AP width. Additionally, the outer edge can further include a posterior curve and an anterior curve, at least a portion of the anterior and posterior curves can extend along the second edge. Further, the anterior curve can have a radius of curvature that is about 75 to about 100 percent the ML width, the posterior curve can have a radius of curvature that is about 70 to about 90 percent the ML width, and the AP width can be about 160 percent to about 190 percent the M-L width, among other ranges.

Such an implant device can also include, among other features, one or more of the following, as well as various combinations thereof: the first edge being configured to be parallel to the midline AP axis of the tibia; the first edge being angled anterior to posterior to the AP axis of the tibia; the first edge having an angled orientation configured to follow the medial edge of the anterior and posterior cruciate ligaments; and/or the anterior and posterior curves being joined by a transition surface that is posterior of the midline of the AP axis of the tibia and which extends for a length that is about 0 to about 25 percent the ML width.

Another aspect of an embodiment of the present application is an implant device for implantation on a tibia that includes an outer edge having a first edge, a second edge, an anterior edge, and a posterior edge. At least a portion of the first and second edges can be separated by a ML width, and at least a. portion of the anterior and posterior edges can be separated by an AP width. Further, the outer edge of the implant device can further include a posterior curve, a medial curve, and an anterior curve, at least a portion of the anterior, medial, and posterior curves extending along the second edge. Additionally, the anterior curve can have a radius of curvature that is about 75 to about 100 percent the ML width, and the anterior curve can extend about 60 to about 80 percent of ML width from the first edge. The. medial curve of. the implant device can also have a radius of curvature that is about 90 to about 110 percent of the ML width, and a tangency of the medial curve to the AP axis of the tibia can be posterior the AP midline and up to 25 percent of the ML width. The posterior curve can have a radius of curvature that is about 70 to about 90 percent the ML width. Additionally, the posterior curve can begin about 0 to about 25 percent of the ML width from the first edge and extend to about 75 percent, but less than 100 percent, of the ML width from the first edge. Further, the AP width can be about 160 to about 190 percent the ML width.

Such an implant device can also include, among other features, one or more of the following, as well as various combinations thereof: the first edge being configured to be parallel to the midline AP axis of the tibia; the first edge being angled anterior to posterior to the AP axis of the tibia; and/or the first edge having an angled orientation configured to follow the medial edge of the anterior and posterior cruciate ligaments.

Another aspect of an embodiment of the present application is an implant device for implantation on a tibia that includes an outer edge having a first edge, a second edge, an anterior edge, and a posterior edge, at least a portion of the first and second edges can be separated by ML width, and at least a portion of the anterior and posterior edges can be separated by an AP width. The outer edge of the implant device can further include a lateral curve that extends along at least a portion of the second edge. The lateral curve can have a radius of curvature that is about 55 to about 70 percent the ML width. Additionally, the lateral curve can begin within about 10 percent of the ML width from the first edge and the AP width can be about 110 to about 150 percent the ML width.

Such an implant device can also include, among other features, one or more of the following, as well as various combinations thereof: the first edge being configured to be parallel to the midline A-P axis of the tibia; the first edge being angled anterior to posterior to the A-P axis of the tibia; and/or the first edge having an angled orientation configured to follow the lateral edge of the anterior and posterior cruciate ligaments.

Another aspect of an embodiment of the present application is an implant device for implantation on a tibia that includes an outer edge having a first edge, a second edge, an anterior edge, and a posterior edge, at least a portion of the first and second edges can be separated by ML width, and at least a portion of the anterior and posterior edges can be separated by an AP width. Additionally, the outer edge of the implant device can further include a posterior curve, a lateral curve, and an anterior curve, at least a portion of the anterior, medial, and posterior curves extending along the second edge. The anterior curve can begin within about 20 percent of the ML width from the medial edge and extend to the lateral curve and can have a radius larger than the lateral curve up to and including an infinite radius. Additionally, the lateral curve can begin at a junction with the posterior curve, extend through the tangency with the second edge, and end at the junction of the anterior curve between about 30 to about 75 percent of the ML width from the first edge. The tangency of the lateral curve with the midline of the first edge can be within about 0 to about 20 percent of the ML width posterior of the midline. Further, the posterior curve can have a radius of curvature that is smaller than the radius of curvature of the anterior and lateral curves. The posterior curve can begin about 20 percent of the ML width from the first edge and extend to about 75 percent, but less than 100 percent, of the ML width from the first edge. Additionally, the AP width can be about 110 percent to about 150 percent the ML width.

Such an implant device can also include, among other features, one or more of the following, as well as various combinations thereof: the first edge being configured to be parallel to the midline AP axis of the tibia; the first edge being angled anterior to posterior to the. AP axis of the tibia; and/or the first edge having an angled orientation configured to follow the lateral edge of the anterior and posterior cruciate ligaments.

Another aspect of an embodiment of the present application is an implant device for implantation on a tibia that includes an outer edge having a first edge, a second edge, an anterior edge, and a posterior edge, at least a portion of the first and second edges being separated by ML width, and at least a portion of the anterior and posterior edges being separated by an AP width. The outer edge can further include a posterior curve, two lateral curves, and an anterior curve, at least a portion of the anterior, lateral, and posterior curves extending along the second edge. The anterior curve can begin within about 20 percent of the ML width from the medial edge, extend to the lateral curve, and have a radius larger than the lateral curve up to and including an infinite radius. The two lateral curves can begin at a junction with the posterior curve, extend through the tangency with the second edge, and end at the junction of the anterior curve between about 10 to about 60 percent of the ML width from the anterior edge. The two lateral curves can be composed of either one or two sections, the two lateral curves each having a radius that is larger than the radius of curvature of the posterior and anterior curves, and the tangency of the two lateral curves with the midline of the second edge being within about 0 to about 20 percent of the ML width posterior of the midline. The posterior curve can begin about 10 to about 60 percent of the ML width from the first edge. The posterior curve can be joined to the first edge by a relatively straight surface or a curve having a radius that exceeds the two lateral curves, and extend to about 75 percent, but less than 100 percent, of the ML width from the first edge. The AP width can be about 110 to about 150 percent the ML width.

Such an implant device can also include, among other features, one or more of the following, as well as various combinations thereof: the first edge can be configured to be parallel to the midline AP axis of the tibia; the first edge can be angled anterior to posterior to the AP axis of the tibia; and/or the first edge can have an angled orientation configured to follow the lateral edge of the anterior and posterior cruciate ligaments.

Another aspect of an embodiment of the present application is an implant device for implantation on a tibia that includes an outer edge having a first edge, a second edge, an anterior edge, and a posterior edge, at least a portion of the first and second edges being separated by ML width, and at least a portion of the anterior and posterior edges being separated by an AP width. An end of the first edge can be angled anterior to posterior to the AP axis of the tibia to provide an end of the first edge adjacent to the posterior edge at a posterior offset position. The outer edge can further include a posterior curve, a lateral curve, and an anterior curve, at least a portion of the anterior, lateral, and posterior curves can extend along the second edge. The anterior curve can begin within about 20 percent of the ML width from the first edge, extends to the lateral curve, and have a radius that is larger than the lateral curve up to and including an infinite radius. The lateral curve can begin at a junction with the posterior curve, extend through the tangency with the second edge, and end at the junction of the anterior curve between about 40 to about 100 percent of the ML width from the first edge. The radius of curvature of the lateral curve can be smaller than the radii of curvature of the anterior and posterior curves. The tangency of the lateral curve with the midline of the first edge can be within about 0 to about 20 percent of the ML width posterior of the midline. The posterior curve can have a radius of curvature that is smaller than the radius of curvature of the anterior curve and larger than the lateral curve. The posterior curve can extend to about 70 to about 100 percent of the ML width from the first edge, and the AP width can be about 110 to about 150 percent the ML width. The first edge of such an implant device can also have an angled orientation that is configured to follow the lateral edge of the anterior and posterior cruciate ligaments.

Another aspect of an embodiment of the present application is an implant device for implantation on a tibia that includes an outer edge having a first edge, a second edge, an anterior edge, and a posterior edge. At least a portion of the first and second edges can be separated by a ML width, and at least a portion of the anterior and posterior edges can be separated by an AP width. The outer edge can further include a posterior curve, a lateral curve, and an anterior curve, at least a portion of the anterior, lateral, and posterior curves can extend along the second edge. The anterior curve can begin within about 20 percent of the ML width from the medial edge, extend to the lateral curve, and have a radius that is larger than the lateral curve, up to and including an infinite radius. The lateral curve can begin at a junction with the posterior curve, extend through the tangency with the second edge, and end at the junction of the anterior curve between about 40 to about 60 percent of the ML width from the first edge. The tangency of the lateral curve with the midline of the first edge can be within about 0 to about 20 percent of the ML width posterior of the midline. The posterior curve can have a radius of curvature that is smaller than the radius of curvature of the anterior and lateral curves. The posterior curve can begin about 20 percent of the ML width from the first edge and extend to about 40 to about 60 percent of the ML width from the first edge. The radius of curvature of the posterior curve can be smaller than the radii of curvature of the anterior and lateral curves. Additionally, the AP width can be about 110 percent to about 150 percent the ML width.

Such an implant device can also include, among other features, one or more of the following, as well as various combinations thereof: first edge can be configured to be parallel to the midline AP axis of the tibia; the first edge can be angled anterior to posterior to the AP axis of the tibia, or the first edge can have an angled orientation that is configured to follow the lateral edge of the anterior and posterior cruciate ligaments.

Another aspect of an embodiment of the present application is an implant device for implantation on a tibia having an outer edge that includes a first edge, a second edge, an anterior edge, and a posterior edge, at least a portion of the first and second edges being separated by ML width, and at least a portion of the anterior and posterior edges being separated by an AP width. The outer edge further includes a posterior curve, two lateral curves, and an anterior curve, at least a portion of the anterior, lateral, and posterior curves extending along the second edge. The anterior curve begins within about 20 percent of the ML width from the medial edge, extends to one of the two lateral curves, and has a radius larger than the lateral curve up to and including an infinite radius. The anterior curve can be coupled to the first edge by a portion of the anterior edge that is acute or at a right angle to the first edge. The two medial curves can begin at a junction with the posterior curve, extend through the tangency with the second edge of the first edge, and end at the junction of the anterior curve between about 20 to about 50 percent of the ML width from the anterior edge. The tangency of the two lateral curves with the midline of the second edge can be within about 0 to about 20 percent of the ML width posterior of the midline. The posterior curve can begin extending from about the first edge to a distance about 20 percent of the ML width from the first edge. The posterior curve can have a radius that is smaller than the radii of curvature of the two lateral curves, and the AP width can be about 110 percent to about 150 percent the ML width.

Such an implant device can also include, among other features, one or more of the following, as well as various combinations thereof: the first edge being configured to be parallel to the midline AP axis of the tibia; the first edge being angled anterior to posterior to the AP axis of the tibia; and/or the first edge having an angled orientation that is configured to follow the lateral edge of the anterior and posterior cruciate ligaments.

Another aspect of an embodiment of the present application is an implant device for implantation on a tibia that includes an outer edge having a first edge, a second edge, an anterior edge, and a posterior edge, at least a portion of the first and second edges being separated by ML width, and at least a portion of the anterior and posterior edges being separated by an AP width. An end of the first edge can be angled anterior to posterior to the AP axis of the tibia to provide an end of the first edge adjacent to the posterior edge at a posterior offset position. The outer edge can further include a posterior curve, a lateral curve, and an anterior, curve, at least a portion of the anterior, lateral, and posterior curves can extend along the second edge. The anterior curve can begin within about 20 percent of the ML width from the medial edge, extend to the lateral curve, and have a radius that is larger than the lateral curve. The lateral curve can begin at a junction with the posterior curve, extend through the tangency with the second edge, and end at the junction of the anterior curve between about 40 to about 60 percent of the ML width from the first edge. The tangency of the lateral curve with the midline of the first edge can be within about 0 to about 20 percent of the ML width posterior of the midline. The posterior curve can have a radius of curvature that is smaller than the radius of curvature of the anterior and lateral curves. The posterior curve can begin about 25 to about 35 percent of the ML width from the offset end of the first edge. The posterior curve and first end can be joined by a transition surface that is angled in the posterior direction. The radius of curvature of the posterior curve can be smaller than the radii of curvature of the anterior and lateral curves, and the AP width can be about 110 percent to about 150 percent the ML width. The first edge of such an implant device can also have an angled orientation that is configured to follow the lateral edge of the anterior and posterior cruciate ligaments.

While the invention has been described in connection with what is presently considered to be the most practical and preferred embodiment, it is to be understood that the invention is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore it should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

The invention claimed is:

1. An implant for implantation on a tibia, comprising:
an outer edge including a first edge, a second edge, an anterior edge, and a posterior edge, at least a portion of the first and second edges being separated by ML width, at least a portion of the anterior and posterior edges being separated by an AP width;
wherein the outer edge comprises at least one curve including a posterior curve, an anterior curve, and a medial curve positioned between the anterior curve and the posterior curve, at least a portion of the anterior and posterior curves extending along at least a portion of the second edge;
wherein the AP width is about 160 percent to about 190 percent the ML width and
wherein the medial curve includes a radius of curvature that is greater than a radius of curvature of the posterior curve but less than a radius of curvature of the anterior curve.

2. The implant of claim 1, wherein the medial curve has a radius of curvature of approximately 90 to approximately 110 percent of the ML width.

3. The implant of claim 1, wherein the medial curve is positioned posteriorly offset from a midline of an AP axis of the tibia and extends for a length that is about 0 percent to about 25 percent of the ML width.

4. The implant of claim 1, further comprising a first curve transition surface positioned between the anterior curve and the first edge and a second curve transition surface positioned between the posterior curve and the first edge.

5. The implant of claim 1, wherein the anterior curve has a radius of curvature of approximately 75 percent to approximately 100 percent the ML width.

6. The implant of claim 5, wherein the anterior curve extends about 60 to about 80 percent of ML width from the first edge.

7. The implant of claim 1, wherein the posterior curve has a radius of curvature of approximately 70 to approximately 90 percent the ML width.

8. The implant of claim 1, wherein the posterior curve extends to about 75 percent to 100 percent of the ML width from the first edge.

9. The implant of claim 1, wherein the anterior curve extends about 60 to about 80 percent of the ML width from the first edge.

10. An implant for implantation on a tibia, comprising:
an outer edge including a first edge, a second edge, an anterior edge, and a posterior edge, at least a portion of the first and second edges being separated by ML width, at least a portion of the anterior and posterior edges being separated by an AP width;
wherein the outer edge comprises at least one curve including a posterior curve and an anterior curve, at least a portion of the anterior and posterior curves extending along at least a portion of the second edge;
wherein the AP width is about 160 percent to about 190 percent the ML width; and
wherein the second edge includes a transition curve positioned along at a least a portion of the second edge, the transition curve positioned between the posterior curve and the anterior curve, the transition curve including a radius of curvature of approximately 90 to approximately 110 percent of the ML width.

11. The implant of claim 10, wherein the transition curve comprises a medial curve, the radius of curvature of the medial curve being greater than a radius of curvature of the posterior curve but less than a radius of curvature of the anterior curve.

12. The implant of claim 11, wherein the medial curve is positioned posteriorly offset from a midline of an AP axis of the tibia and extends for a length that is about 0 percent to about 25 percent of the ML width.

13. The implant of claim 11, wherein the posterior curve has a radius of curvature of approximately 70 to approximately 90 percent the ML width.

14. The implant of claim 10, further comprising a first curve transition surface positioned between the anterior curve and the first edge and a second curve transition surface positioned between the posterior curve and the first edge.

15. The implant of claim 10, wherein the transition curve comprises a lateral curve, the radius of curvature of the lateral curve being greater than a radius of curvature of the posterior curve and a radius of curvature of the anterior curve.

16. An implant for implantation on a tibia, comprising:
an outer edge including a first edge, a second edge, an anterior edge, and a posterior edge, at least a portion of the first and second edges being separated by ML width, at least a portion of the anterior and posterior edges being separated by an AP width;
wherein the outer edge comprises at least one curve including a posterior curve and an anterior curve, at least a portion of the anterior and posterior curves extending along at least a portion of the second edge;
wherein the AP width is about 160 percent to about 190 percent the ML width; and
wherein the posterior curve has a radius of curvature of approximately 70 to approximately 90 percent the ML width.

17. The implant of claim 16, wherein the second edge includes a transition curve positioned along at a least a portion of the second edge, the transition curve positioned between the posterior curve and the anterior curve, the transition curve including a radius of curvature of approximately 90 to approximately 110 percent of the ML width.

18. The implant of claim 16, wherein the at least one curve comprises a medial curve positioned between the anterior curve and the posterior curve, the medial curve including a radius of curvature that is greater than a radius of curvature of the posterior curve but less than a radius of curvature of the anterior curve.

19. The implant of claim 18, wherein the medial curve is positioned posteriorly offset from a midline of an AP axis of the tibia and extends for a length that is about 0 percent to about 25 percent of the ML width.

20. The implant of claim 16, further comprising a first curve transition surface positioned between the anterior curve and the first edge and a second curve transition surface positioned between the posterior curve and the first edge.

\* \* \* \* \*